United States Patent [19]

Chen et al.

[11] Patent Number: 5,800,478
[45] Date of Patent: Sep. 1, 1998

[54] FLEXIBLE MICROCIRCUITS FOR INTERNAL LIGHT THERAPY

[75] Inventors: James C. Chen, Bellevue, Wash.; Brent Wiscombe, Mesa, Ariz.

[73] Assignee: Light Sciences Limited Partnership, Issaquah, Wash.

[21] Appl. No.: 613,390

[22] Filed: Mar. 7, 1996

[51] Int. Cl.$^6$ .................................................. A61N 5/00
[52] U.S. Cl. .................................. 607/88; 607/92; 606/14
[58] Field of Search .............................. 607/88, 89, 90, 607/92, 116, 152, 129; 606/14, 15, 16, 17, 10; 604/19, 20, 21; 600/373–375, 377

[56] References Cited

U.S. PATENT DOCUMENTS

| | | | |
|---|---|---|---|
| 1,384,467 | 7/1921 | Homan | 607/152 |
| 4,634,631 | 1/1987 | Gazit et al. | 428/421 |
| 4,647,508 | 3/1987 | Gazit et al. | 428/421 |
| 4,761,047 | 8/1988 | Mori | 607/88 |
| 4,804,240 | 2/1989 | Mori | 607/92 |
| 4,930,504 | 6/1990 | Diamantopoulos et al. | 607/88 |
| 5,324,322 | 6/1994 | Grill, Jr. et al. | 607/118 |
| 5,358,503 | 10/1994 | Bertwell et al. | 607/88 |
| 5,445,608 | 8/1995 | Chen et al. | 604/20 |
| 5,505,730 | 4/1996 | Edwards | 606/41 |
| 5,571,152 | 11/1996 | Chen et al. | 607/92 |
| 5,603,732 | 2/1997 | Dahl et al. | 607/129 |
| 5,616,140 | 4/1997 | Prescott | 606/10 |
| 5,741,322 | 4/1998 | Mehmanesh et al. | 607/129 |

FOREIGN PATENT DOCUMENTS

WO 93/21842  11/1993  WIPO .

OTHER PUBLICATIONS

Barth et al., "Monolithic Silicon Fabrication Technology for Flexible Circuit and Sensor Arrays," pp. 83–86.
Schmidt et al., "Light–emitting Diodes as a Light Source for Intraoperative Photodynamic Therapy," *Neurosurgery*, vol. 38, No. 3, Mar. 1996, pp. 552–557.
Gomez, "Ultrasonic Ventriculostomy Stylet," *Neurosurgery*, vol. 37, No. 5, Nov. 1995, pp. 1020–1021.

*Primary Examiner*—Jennifer Bahr
*Assistant Examiner*—Bryan K. Yarnell
*Attorney, Agent, or Firm*—Ronald M. Anderson

[57] ABSTRACT

A plurality of embodiments for a flexible probe used to provide photodynamic therapy (PDT) and to effect other medical procedures at an internal treatment site inside a patient's body. Each of the embodiments of the flexible probe (100, 108, 130, 158, 182, 190, 220, 280, 370, 390, 440, 460, 520) includes a flexible substrate (102, 184, 196, 222, 250, 282, 412, 462, 482, 502, 522) on which are disposed conductive traces (414, 466, 468, 488, 490, 504, 506, 524, 526) electrically connected to leads through which electrical current and signals are conveyed. A plurality of light sources (104, 192, 256, 286, 418, 436, 470, 492, 508, 542) or other micro-electronic circuits are connected to the conductive traces and mounted on the flexible substrate. Each of the embodiments of the flexible probes is enclosed within a transparent, biocompatible polymer envelope (106, 110, 464, 522). Due to the characteristic elastic properties of the flexible substrate, the flexible probe can readily be bent, folded, or rolled while being disposed at the internal treatment site, thereby enabling the probe to pass through a guide tube (120), an incision, a catheter (150), or a lumen (154) of relatively small cross-sectional diameter. Once disposed at the treatment site, a folded or rolled flexible probe can be unfolded or unrolled to supply light for PDT, or energized to provide other types of medical treatment.

51 Claims, 27 Drawing Sheets

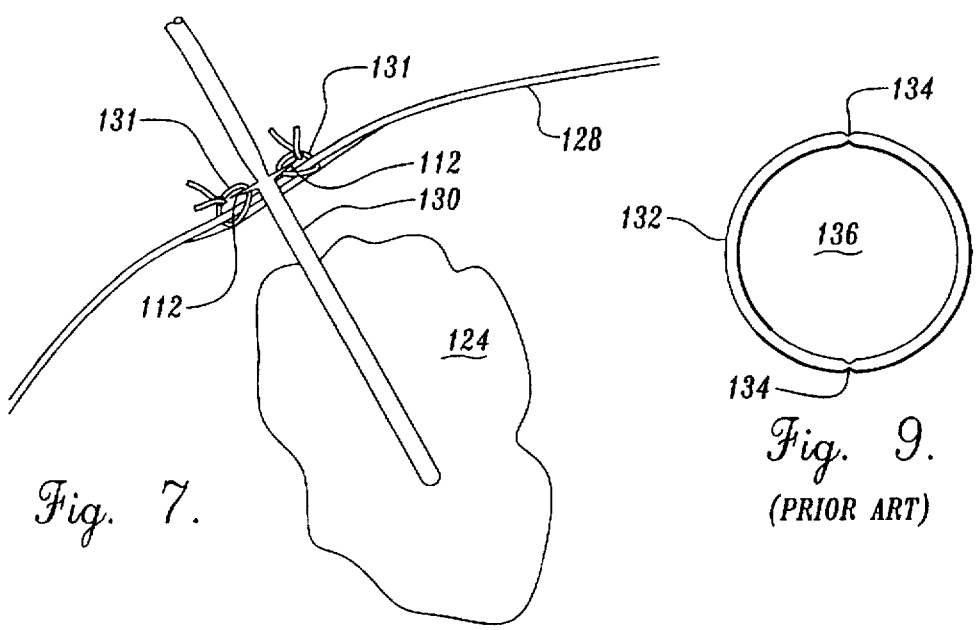
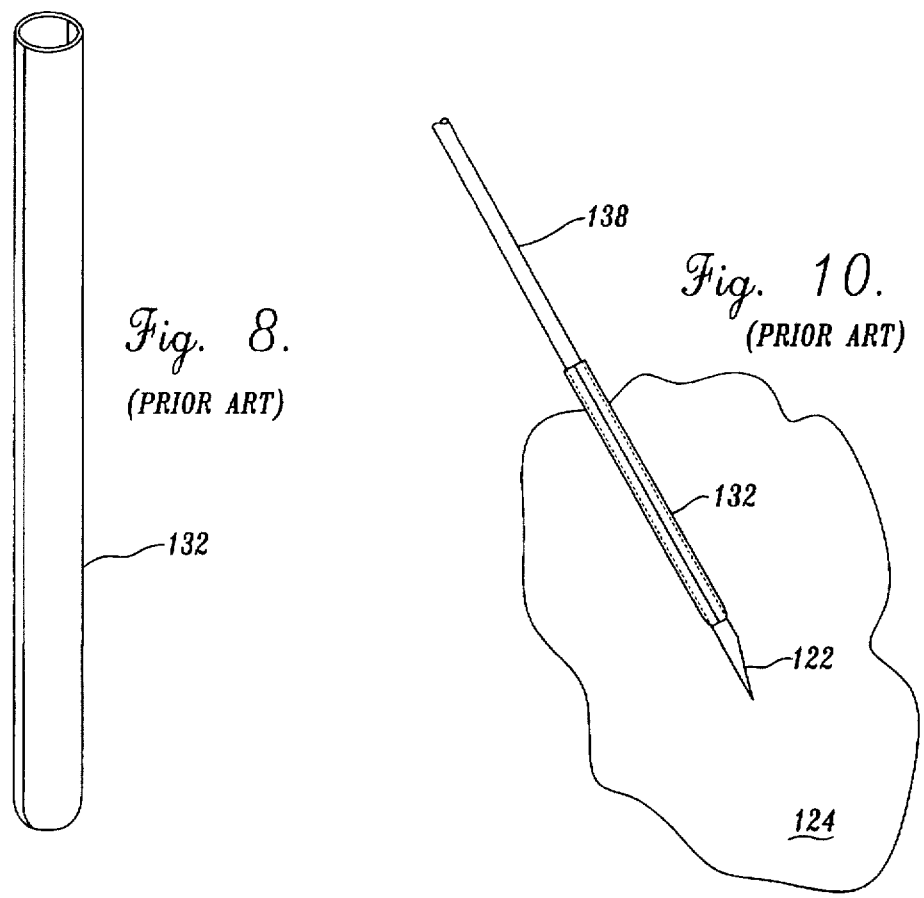

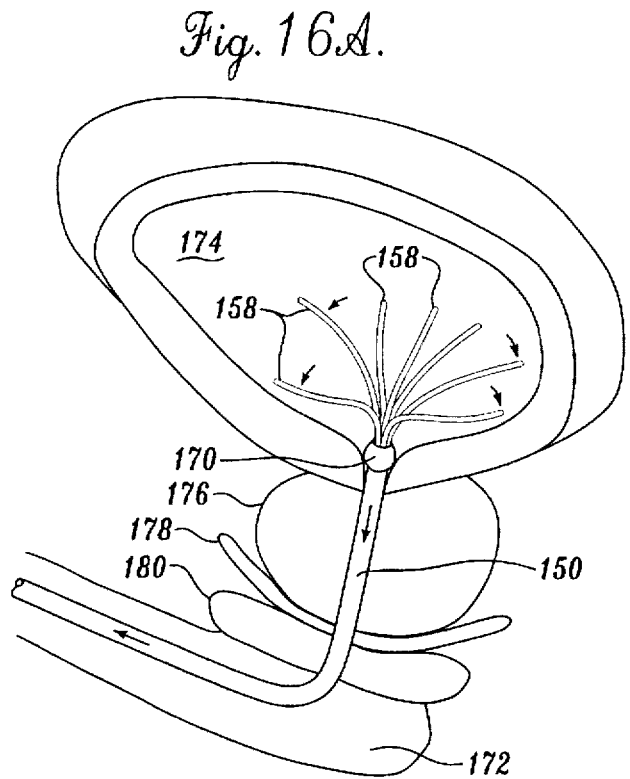
Fig. 16A.
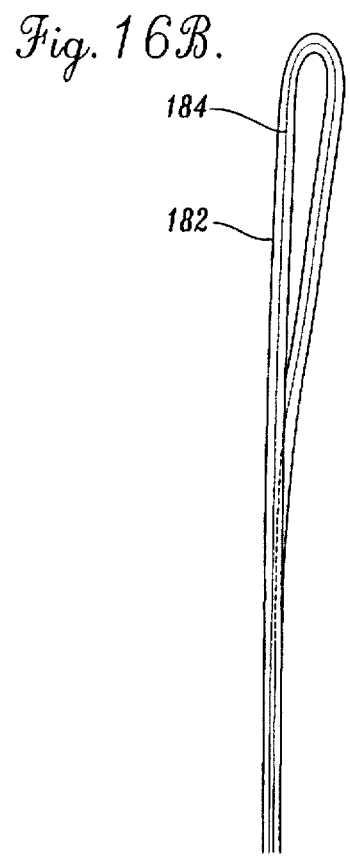
Fig. 16B.
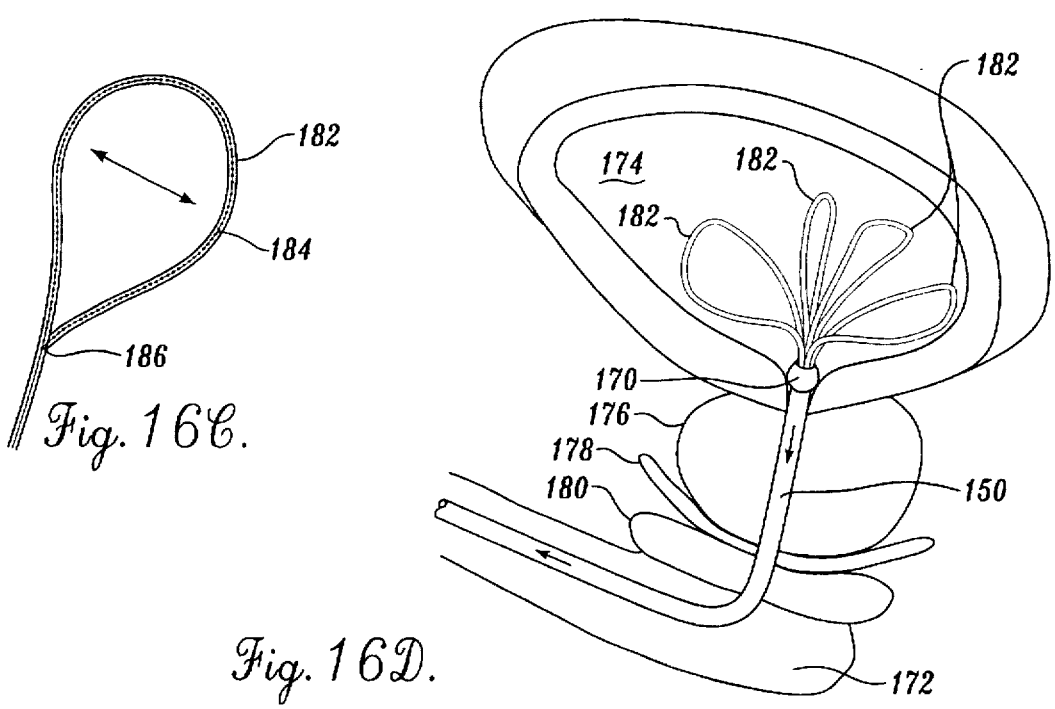
Fig. 16C.
Fig. 16D.

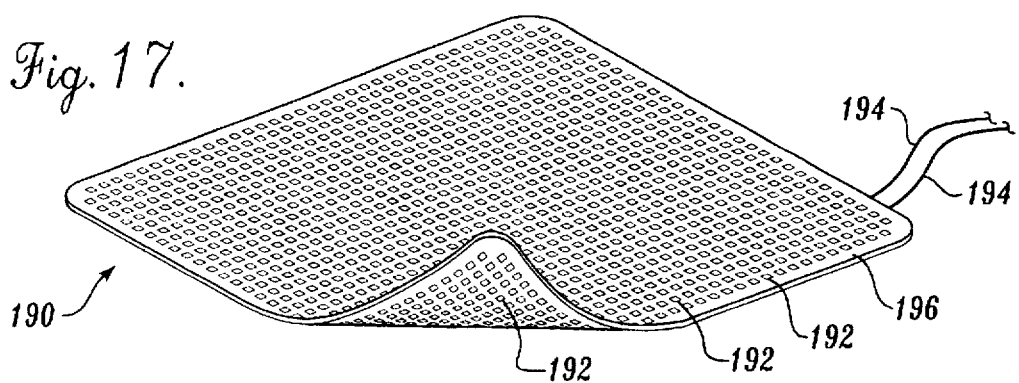
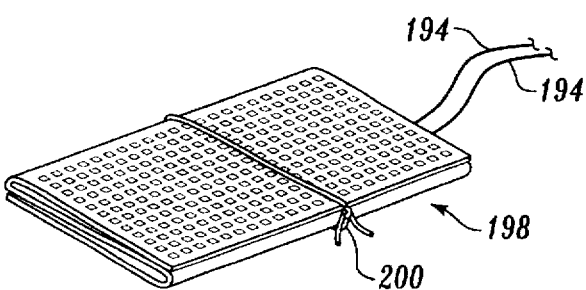
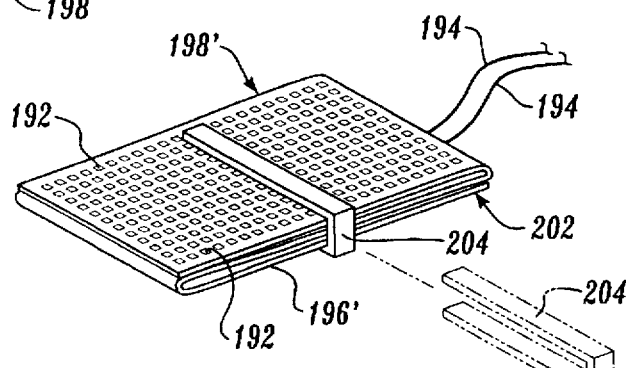
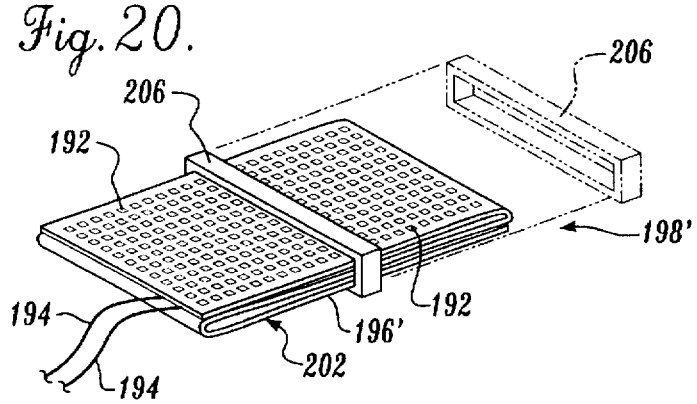
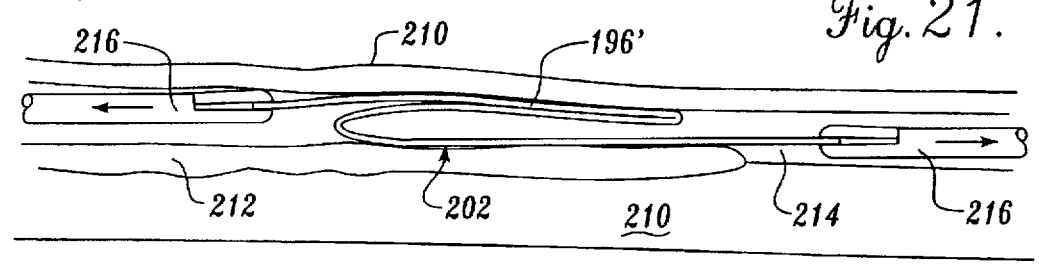

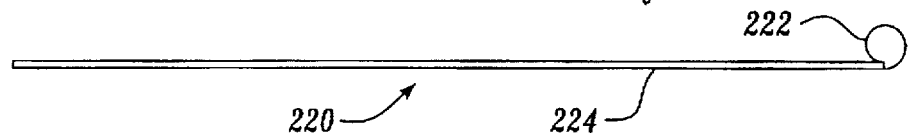
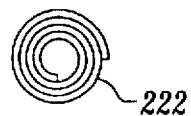
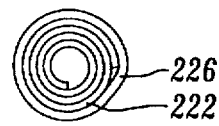
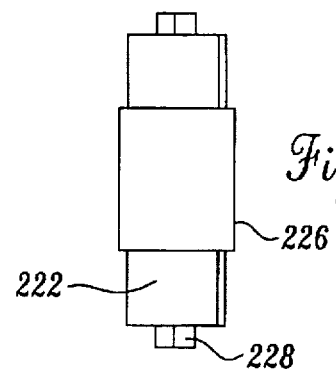
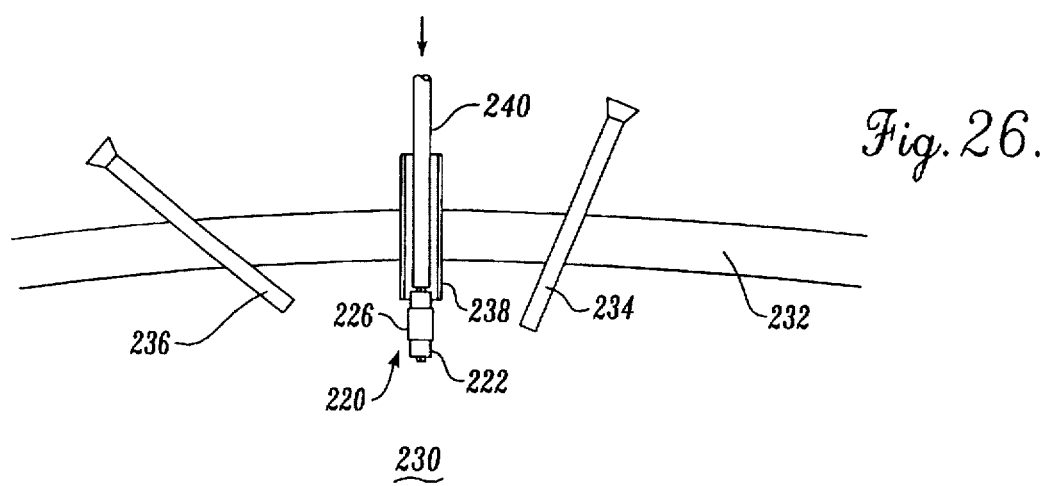

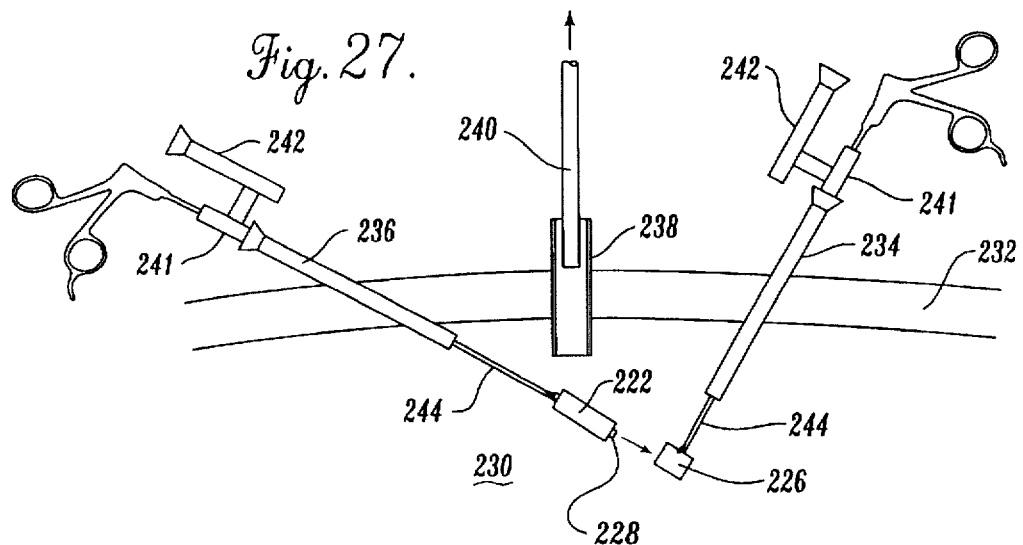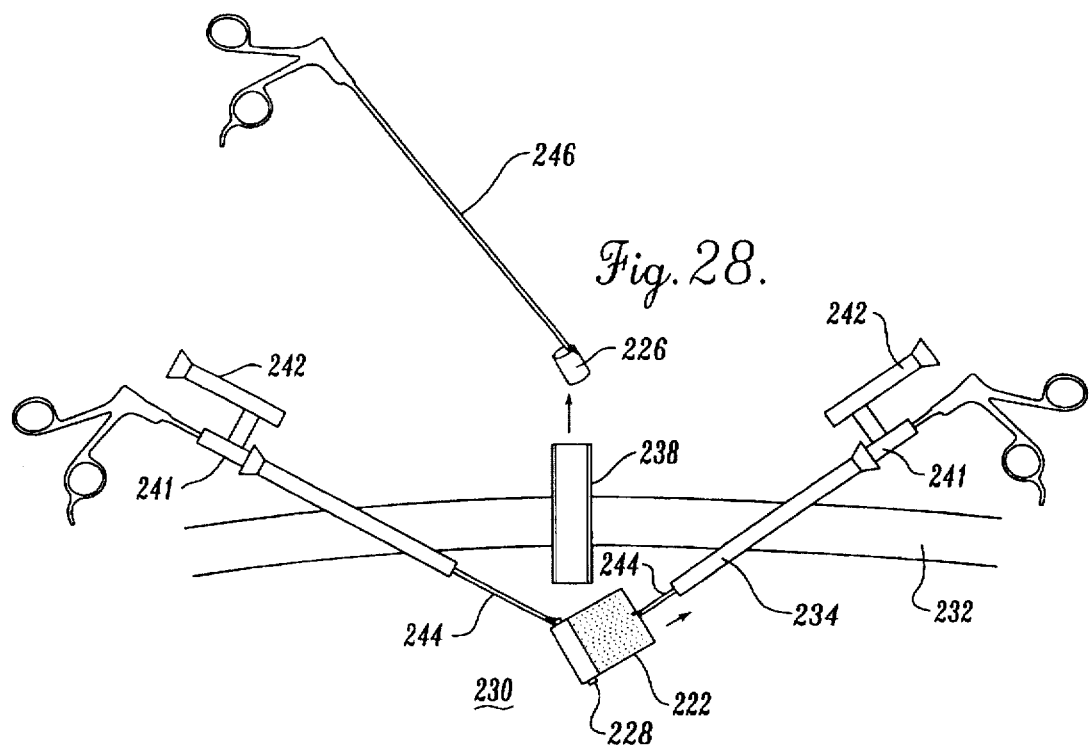

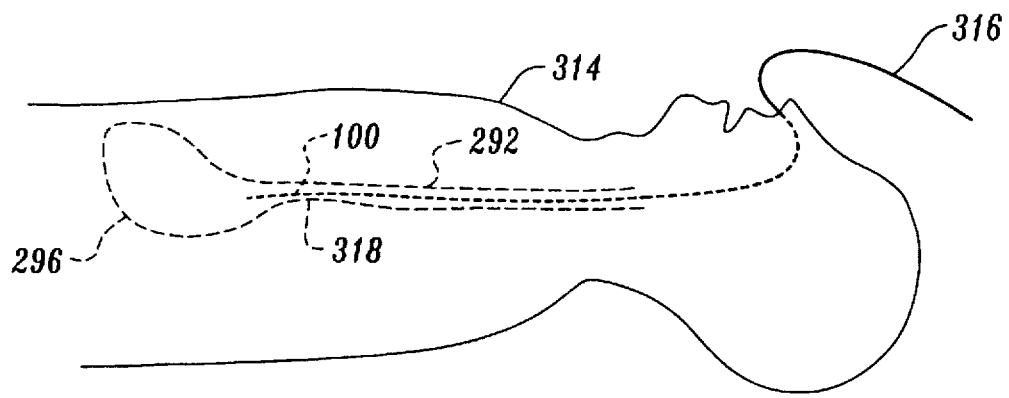
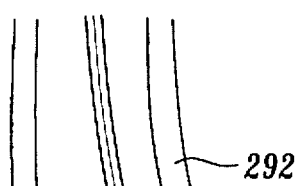
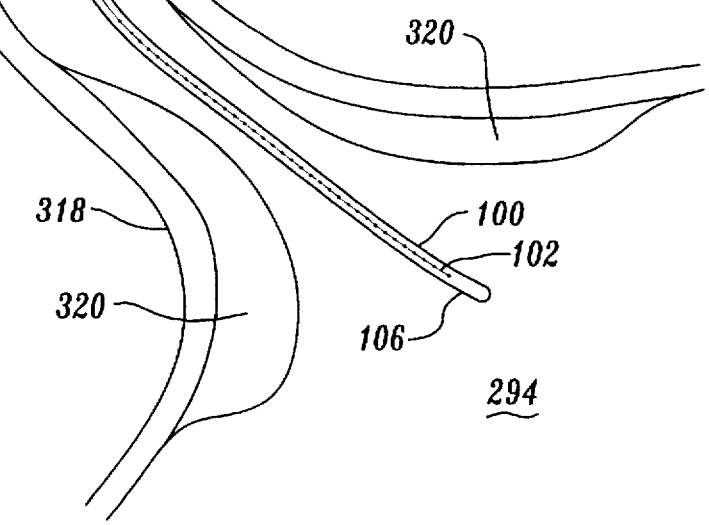

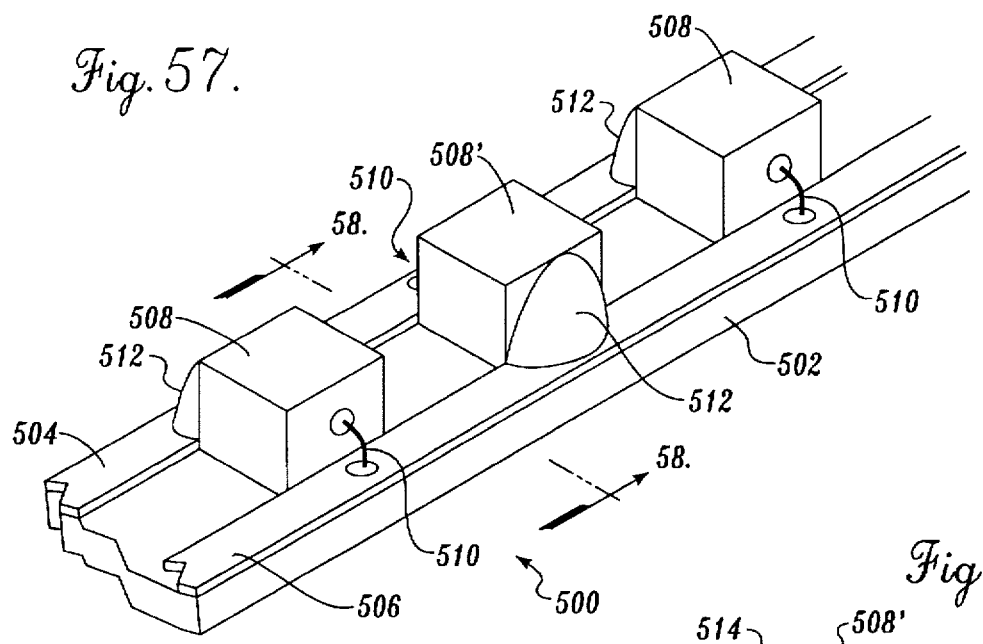
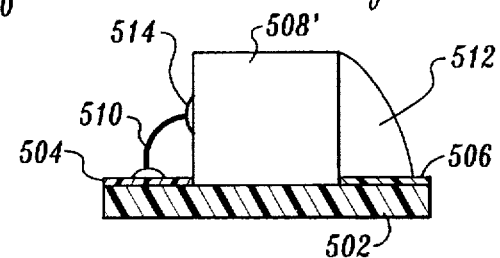
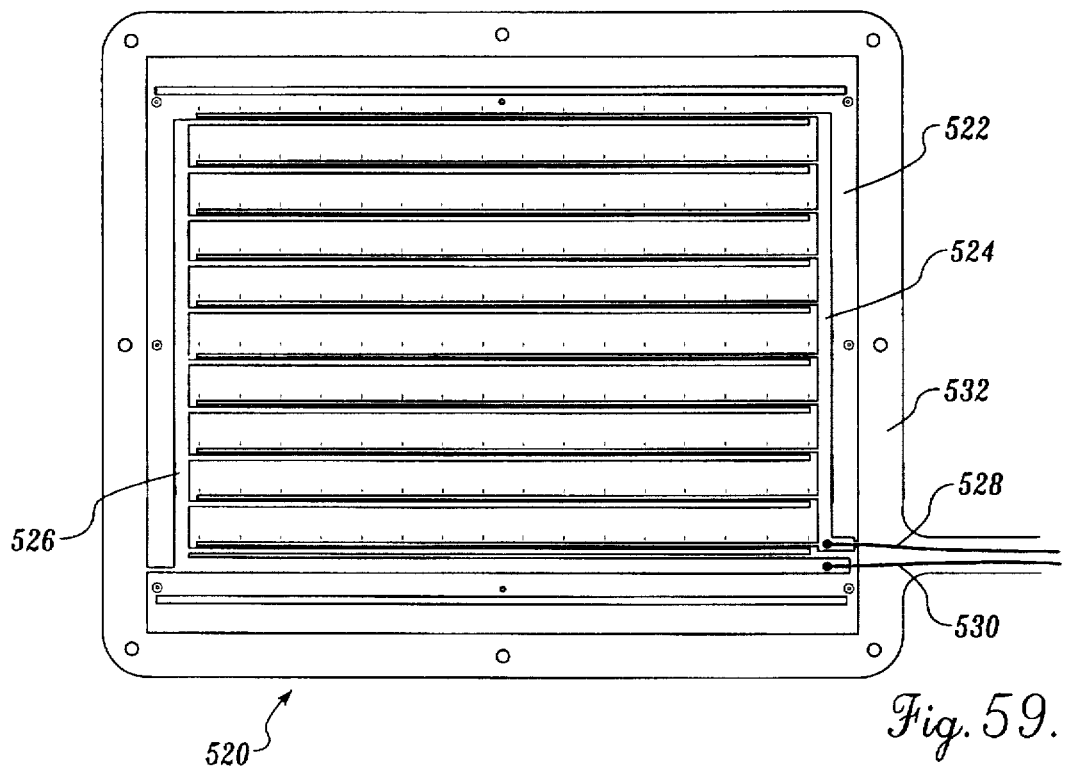

FLEXIBLE MICROCIRCUITS FOR INTERNAL LIGHT THERAPY

FIELD OF THE INVENTION

This invention generally relates to a fixture on which is disposed an electronic device used in a medical procedure that is effected by insertion of the fixture into a patient's body, and more specifically, to a probe adapted for insertion into a patient's body through an incision or natural body opening, to implement the medical procedure at a site within the patient's body.

BACKGROUND OF THE INVENTION

Abnormal cells in the body are known to selectively absorb certain dyes perfused into a treatment site to a much greater extent than surrounding tissue. For example, tumors of the pancreas and colon may absorb two to three times the volume of certain dyes, compared to normal cells. Once pre-sensitized by dye tagging, the cancerous or abnormal cells can be destroyed by irradiation with light of an appropriate wavelength or waveband corresponding to an absorbing wavelength or waveband of the dye, with minimal damage to normal tissue. This procedure, which is known as photodynamic therapy (PDT), has been clinically used to treat metastatic breast cancer, bladder cancer, lung carcinomas, esophageal cancer, basal cell carcinoma, malignant melanoma, ocular tumors, head and neck cancers, and other types of malignant tumors. Because PDT may selectively destroy abnormal cells that have absorbed more of the dye than normal cells, it can successfully be used to kill malignant tissue with less effect on surrounding benign tissue than alternative treatment procedures.

Typically, invasive applications of PDT have been used during surgical procedures employed to gain access to a treatment site inside the body of the patient to administer light produced by relatively high intensity light sources. Optical fibers in a hand-held probe are often used to deliver the intense light to the surgically exposed treatment site from a remote source to reduce damage to surrounding tissue from the heat developed by the light source. High power lasers or solid state laser diode (LD) arrays in a remote light source coupled to the optical fibers are normally used for the light source.

It has been shown possible, in certain cases, to obtain improved therapeutic results in PDT at a low light level. As reported by J. A. Parrish in "Photobiologic Consideration in Photoradiation Therapy," pp. 91–108, *Porphyrin Photosensitization*, Plenum Press, (1983), preliminary laboratory studies with hematoporphyrin and visible light suggest that low light intensity light may be more effective in PDT. In these experiments, subcutaneous tumors in the flanks of newborn rats were treated with the same external dose of 620 nm radiation at intensities of 7.5, 28, and 75 mW/cm$^2$. At the same total light dosage, Parrish found that greater tumor necrosis occurred at the lowest light intensity used.

Light emitting probes designed to be transcutaneously introduced into the body of a patient at a desired treatment site, to administer PDT using low light level sources, for extended periods of time, are taught in commonly assigned U.S. Pat. No. 5,445,608, the drawings and disclosure of which are specifically incorporated herein by reference. Several different embodiments of such probes are illustrated and discussed in this patent. Each of the probes disclosed in this reference includes a plurality of light sources that are mounted on a relatively stiff or inflexible substrate and enclosed within a transparent envelope through which light emitted by the light sources is transmitted to the tumor or other cells to be destroyed by the PDT. The light sources used on the probes taught by this reference are preferably light emitting diodes (LEDs). By transcutaneously inserting one of these probes into an internal treatment site and applying PDT over an extended time frame, abnormal cells at the treatment site can be destroyed without adverse impact on normal cells.

None of the implantable light emitting probes disclosed in the above-referenced patent include light sources mounted on flexible substrates. There are many applications for PDT in which it would be advantageous to use a flexible substrate for mounting the LEDs or other light sources on a probe used to administer the PDT, e.g., so that the probe can be threaded into a treatment site through a curved passage within the patient's body without risk of perforation of the passage wall. In contrast to the relatively inflexible substrate used in the probes disclosed in the above-referenced patent, a flexible PDT probe could be folded or rolled into a smaller cross-sectional size for insertion into a treatment site through an incision or body passage and then allowed to deploy, unfolding or unrolling into a larger size for administration of low intensity light to the treatment site. Alternatively, a flexible probe could be molded around an irregularly shaped tumor or organ or rolled around a lumen, such as a blood vessel, or unfurled inside an organ or lumen to irradiate its interior with light emitted by the probe. In addition, a flexible probe would be able to change shape to adapt to changes in the treatment site, as malignant tissue is destroyed by the PDT, and should be able to move with an organ (such as a lung or the heart) or blood vessel, due to a physiological displacement or change in the shape of the organ or vessel, without interfering with the function of the organ or vessel. The prior art does not disclose a flexible probe capable of providing these capabilities.

It is also apparent that a flexible probe could more readily be introduced to a treatment site for implementing medical procedures other than PDT. For example, a flexible probe that includes an ultrasonic transmitter and/or ultrasonic receiver could more readily be inserted into an organ or lumen to carry out an ultrasound scan of surrounding tissue relative to the site inside the organ or lumen. Furthermore, a flexible probe that is used to administer PDT can be provided with electronic components capable of carrying out additional functions. For example, a sensor to determine the efficacy of the PDT treatment might be included on a flexible probe, in addition to the plurality of LEDs or other light sources that are used to provide light to a treatment site.

A flexible probe on which an electronic circuit for administering a medical treatment or a sensing device is mounted can more readily be threaded into an internal site than a rigid or inflexible probe, and the insertion procedure can be implemented with less trauma to a patient. In addition, a flexible probe is less likely to cause an unwanted and potentially harmful perforation, or to move from a treatment site within a patient's body. Thus, there are significant advantages to be realized in using a flexible probe rather than a relatively rigid probe for administering medical treatment or carrying out diagnostic procedures. By inserting a flexible probe into the patient's body through a small incision and threading it to a site where it will be used in a medical procedure, the patient would likely be exposed to less risk of infection and loss of blood than is occasioned by the more extensive surgery used in conventional applications of the treatment. Further, a flexible probe may be left in place at a treatment site longer, due to the minimal impact it has on the patient's normal physiological functions and due to its ability to adjust to changing conditions at the treatment site. For these and other reasons that will be evident from the following disclosure, a flexible probe configured in accord with the present invention offers substantial advantages over prior art approaches to administering PDT and other types of medical treatment to an internal treatment site within a patient's body.

SUMMARY OF THE INVENTION

The present invention is directed to apparatus for effecting a medical treatment at an internal site within a patient's body. The apparatus includes a flexible substrate that serves as a support. A plurality of conductive traces are affixed to the flexible substrate and are sufficiently flexible to bend with the flexible substrate without breaking or separating from the flexible substrate as the flexible substrate is bent during its insertion into a patient's body and advanced to the internal site. An electronic medical device is disposed on the flexible substrate and is coupled to the plurality of conductive traces. The electronic medical device is carried by the flexible substrate for disposition at the internal site. A plurality of electrical leads are connected to the conductive traces. The electrical leads are adapted to couple to a source of electrical power in order to energize the electronic medical device, and are operative to carry signals between the electronic medical device and a different location. A biocompatible flexible envelope encloses the flexible substrate, the plurality of conductive traces, and the electronic medical device.

One embodiment of the flexible substrate comprises a strip having a thickness, a width, and a length. The thickness of the strip is substantially less than its width, and the width of the strip is substantially less than its length. The electronic medical device comprises at least one micro-electronic circuit that is mounted on the strip.

Alternatively, the flexible substrate comprises a sheet having a thickness and a width. The thickness of the sheet is substantially less than its width. In this embodiment, the electronic medical device also comprises at least one microelectronic circuit that is mounted on the sheet.

In one application, the flexible substrate is sufficiently flexible to be rolled into a tubular shape for insertion into the patient's body. When thus rolled, the tubular shape has a substantially smaller transverse cross-sectional dimension than the width of the flexible substrate before being rolled.

Similarly, the flexible substrate is sufficiently flexible to be folded into a more compact shape without damage. In one form of this embodiment, the flexible substrate is folded at about a midpoint, being thereby adapted to form a loop that is collapsed for insertion into the patient's body. At the internal site, the loop opens to form an open loop to provide greater coverage for the electronic device.

Another aspect of the present invention is directed to apparatus for administering light to a treatment site within a patient's body, to provide light therapy to the treatment site. The apparatus includes a flexible substrate that serves as a support. Conductive traces are affixed to the flexible substrate and are sufficiently flexible to bend with the flexible substrate without breaking or separating from the flexible substrate. At least one light source is electrically coupled to the conductive traces and is mounted to the flexible substrate. In addition, a plurality of electrical leads are connected to the conductive traces. The electrical leads are adapted to connect to a source of electrical power in order to energize the one or more light sources.

An envelope of a transparent flexible material generally encloses the one or more light sources, the conductive traces, and the flexible substrate. The flexible envelope transmits light from the one or more light sources to the treatment site.

In one preferred form of the invention, the flexible substrate comprises a sheet that is generally quadrilateral in shape. A plurality of the light sources are spaced apart on the flexible substrate, forming an array. For one configuration of this embodiment, the flexible substrate is folded. In another configuration, the flexible substrate is rolled to minimize its width for insertion within the patient's body and disposition at the treatment site. The flexible substrate is then allowed unroll to administer the light therapy. When the flexible substrate is folded to reduce its cross-sectional area, it is more readily inserted within the patient's body and disposed at the treatment site. At the treatment site, the flexible substrate is unfolded to administer the light therapy.

The apparatus further includes an electromagnetic receiver that is connected to the electrical leads. The electromagnetic receiver is adapted to electromagnetically couple to a source of electrical power that is disposed outside the patient's body, and thus to provide an electrical current for energizing the one or more light sources. Electrical power for energizing the apparatus can be stored in a battery that is charged when the flexible probe is disposed at the treatment site or from power received via the electromagnetic receiver. The electromagnetic receiver preferably comprises an electromagnetic coil. Alternatively, the electromagnetic receiver comprises a radio frequency receiver that receives radio frequency energy transmitted from an external source.

It is also contemplated that power in the form of infra-red (IR) light can be transmitted through a cutaneous layer of a patient's body to an IR detector from an external source of (IR) to supply power. The IR detector, which can be mounted on the flexible substrate or at another site within the patient's body, converts the IR light to electrical current to provide power to the apparatus.

The flexible substrate has a predetermined configuration when not constrained and is thus adapted to be inserted into a treatment site in a restrained configuration and brought into contact with tissue at the treatment site so that the tissue contacts the flexible substrate and maintains the flexible substrate in its restrained configuration. A characteristic elasticity of the flexible substrate adapts it to change shape and flex toward its unconstrained configuration as the tissue at the treatment site shrinks due to the photodynamic therapy. Due to this ability, the flexible substrate changes size and shape as necessary to maintain the light sources in close proximity with the treatment site.

Another aspect of the present invention is directed to a method for administering light therapy to an internal treatment site within a patient's body. The steps of the method are generally consistent with the functions provided by the apparatus discussed above.

Yet another aspect of the present invention concerns apparatus for effecting a medical treatment at an internal site within a patient's body. The apparatus includes a flexible substrate that serves as a support. A plurality of conductive traces are affixed to the flexible substrate and are sufficiently flexible to bend with the flexible substrate without breaking or separating from the flexible substrate. An electronic medical device is disposed on the flexible substrate and is coupled to the plurality of conductive traces. The electronic medical device is carried by the flexible substrate when positioned at the internal site. A plurality of electrical leads are connected to the conductive traces. The electrical leads are adapted to couple to a source of electrical power in order to energize the electronic medical device and carry signals between the electronic medical device and another location.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 7 is a side view showing the flexible probe sutured to a tissue layer to secure the flexible probe in a treatment site;

FIG. 8 is an isometric view of a prior art peel-away sheath;

FIG. 9 is a plan view of the prior art peel-away sheath of FIG. 8;

FIG. 10 is a side view of the prior art peel-away sheath of FIG. 8 and a prior art lancet that is used to position the peel-away sheath in a tissue mass;

FIG. 16A is a sectional view of the bladder, showing the catheter being withdrawn and the plurality of flexible probes splaying apart inside the bladder;

FIG. 16B is a side view of a portion of a fourth embodiment of a flexible probe formed as a loop, shown in a flattened or compressed state;

FIG. 16C is a side view of the fourth embodiment of the flexible probe in an open, uncompressed state;

FIG. 16D is a sectional view of the bladder in which a plurality of probes in accord with the fourth embodiment are shown in a splayed array as the catheter used to introduce the probes into the bladder is withdrawn;

FIG. 17 is an isometric view of a fourth embodiment of the flexible probe configured as a flexible sheet;

FIG. 18 is an isometric view of the fourth embodiment of the flexible probe folded to reduce its transverse size and tied with a suture to restrain it in the folded configuration;

FIG. 19 is an isometric view of the fourth embodiment of the flexible probe folded to reduce its transverse size and clipped with a U-shaped clip to restrain it in the folded configuration;

FIG. 20 is an isometric view of the fourth embodiment of the flexible probe folded to reduce its transverse size and clipped with a rectangular-shaped band to restrain it in the folded configuration;

FIG. 21 is a sectional view of the fourth embodiment of the flexible probe, showing the flexible probe being pulled by forceps from opposite ends to unfold it at a treatment site in a body lumen;

FIG. 22 is a side view of the fourth embodiment of the flexible probe, showing the sheet rolled into a cylindrical configuration;

FIG. 23 is an end view of the rolled flexible probe of FIG. 22;

FIG. 24 is an end view of the rolled flexible probe of FIG. 22, restrained in a cylindrical sleeve;

FIG. 25 is an elevational view of the rolled flexible probe of FIG. 24;

FIG. 26 is a sectional view of a portion of a patient's torso, showing the rolled fourth embodiment being positioned at a treatment site through an access tube that extends through the cutaneous layer;

FIG. 27 is a sectional view of the portion of the torso, showing the restraining sleeve being removed from the rolled flexible probe;

FIG. 28 is a sectional view of a treatment site inside a patient's body, showing the flexible probe being unrolled at the treatment site;

FIG. 33 is a sectional view of a patient's organ showing a fifth embodiment of the flexible probe that includes a

Figure 34:
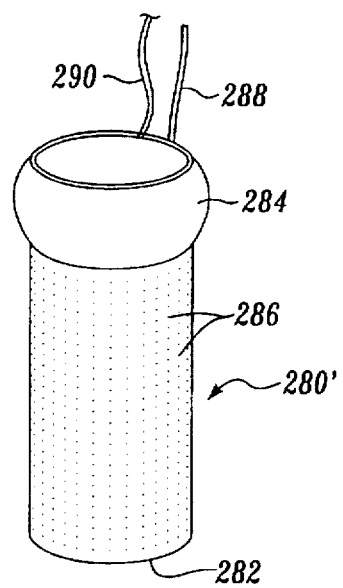
Figure 35:
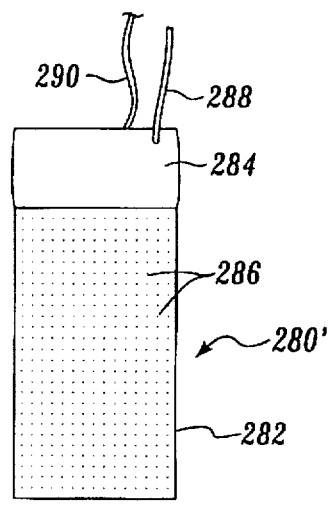
Figure 38:
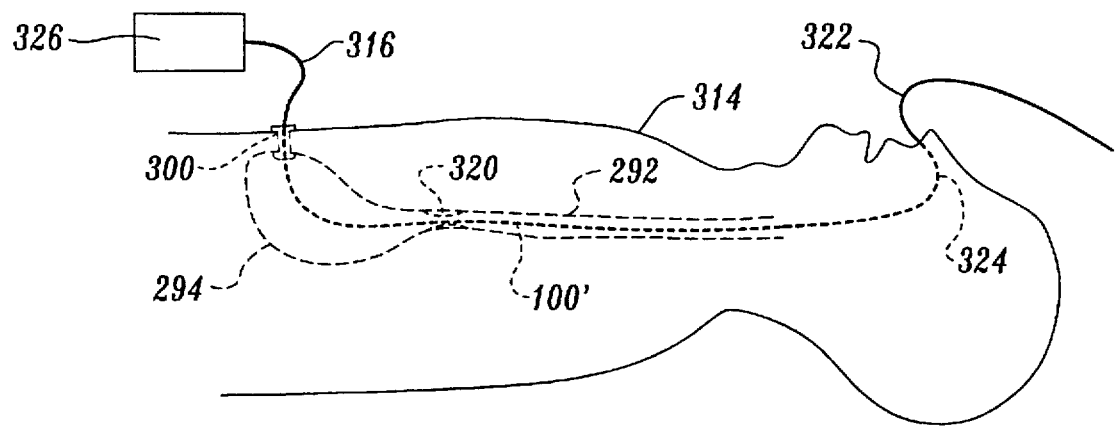
Figure 39:
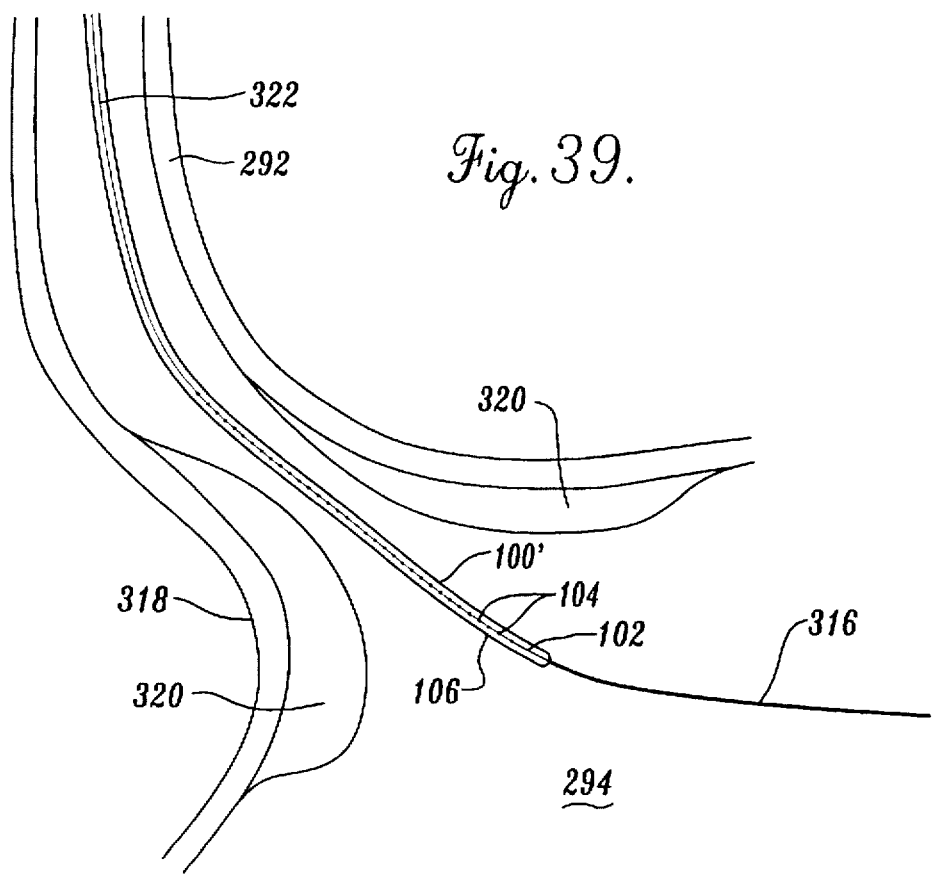
Figure 40:
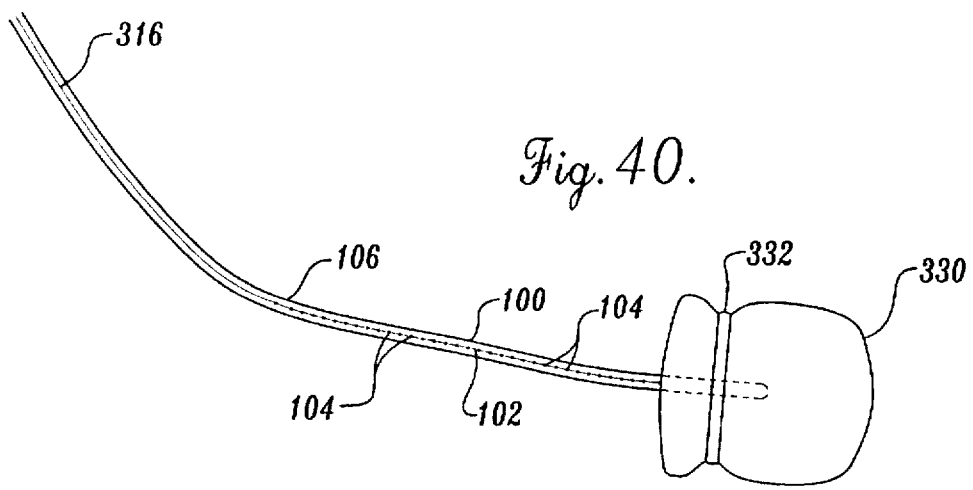
Figure 41:
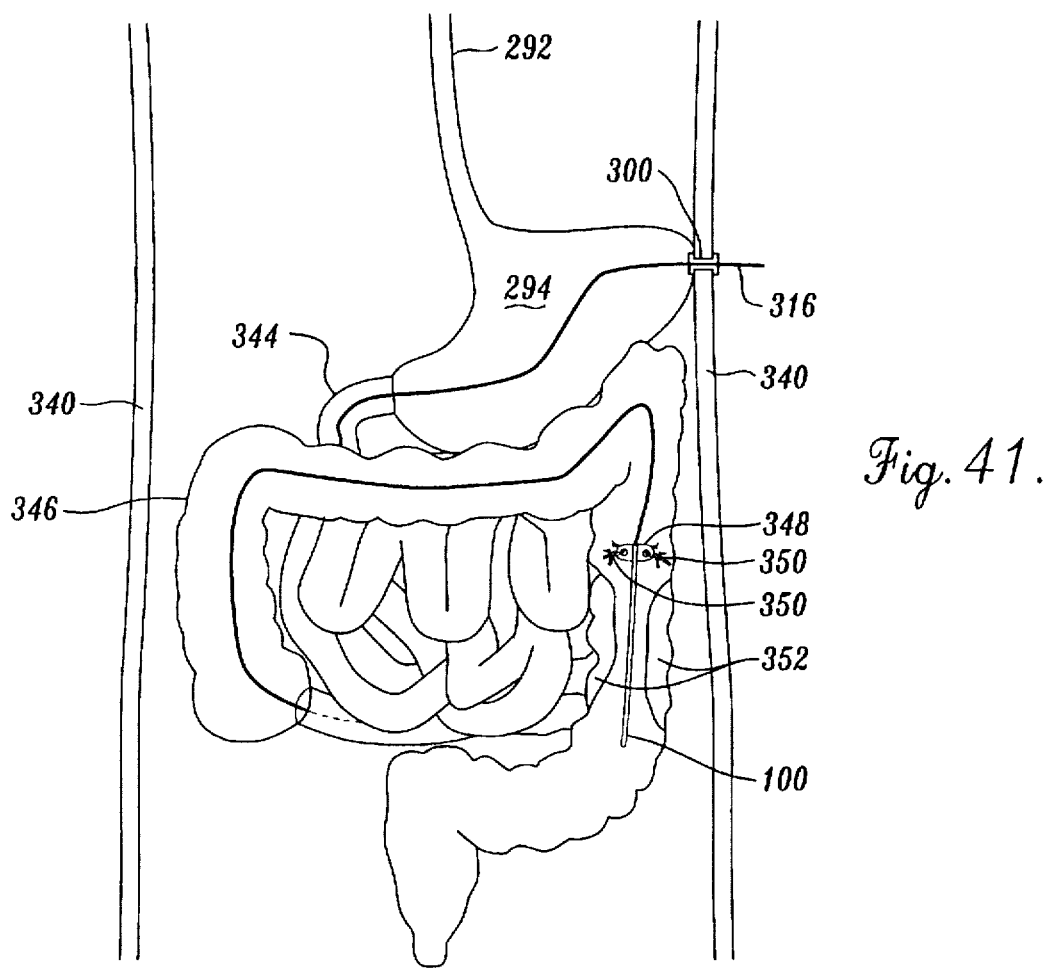
Figure 42:
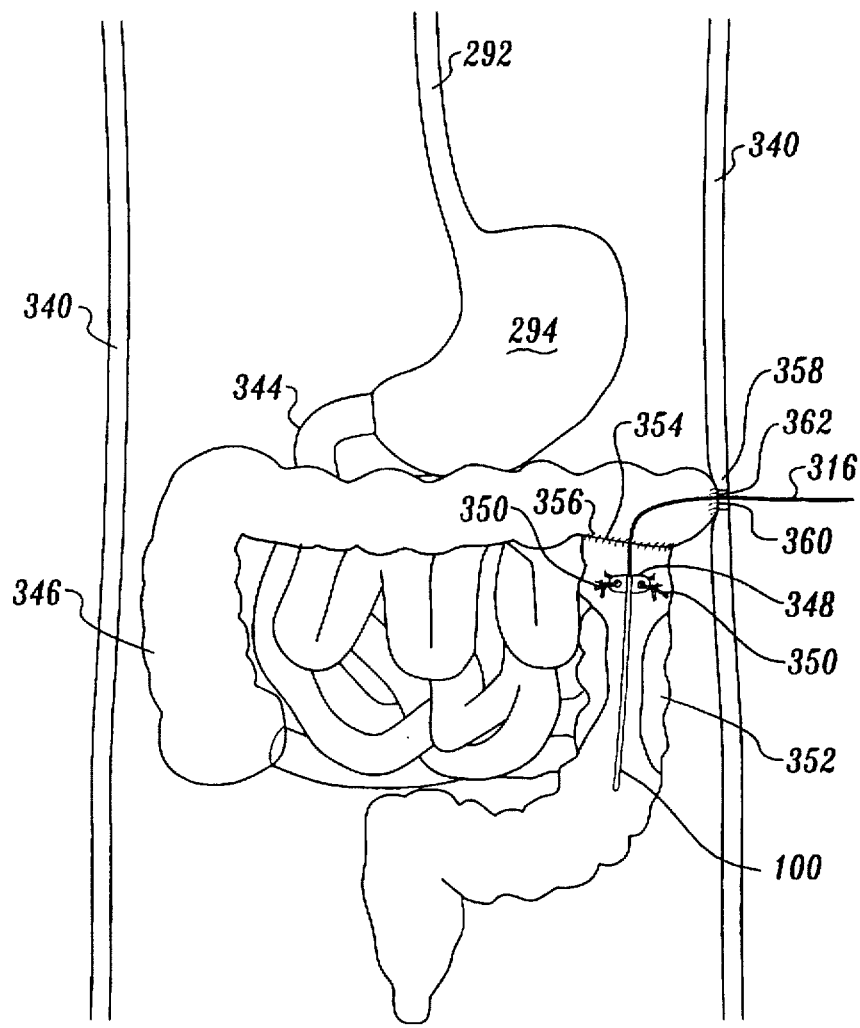
Figure 43:
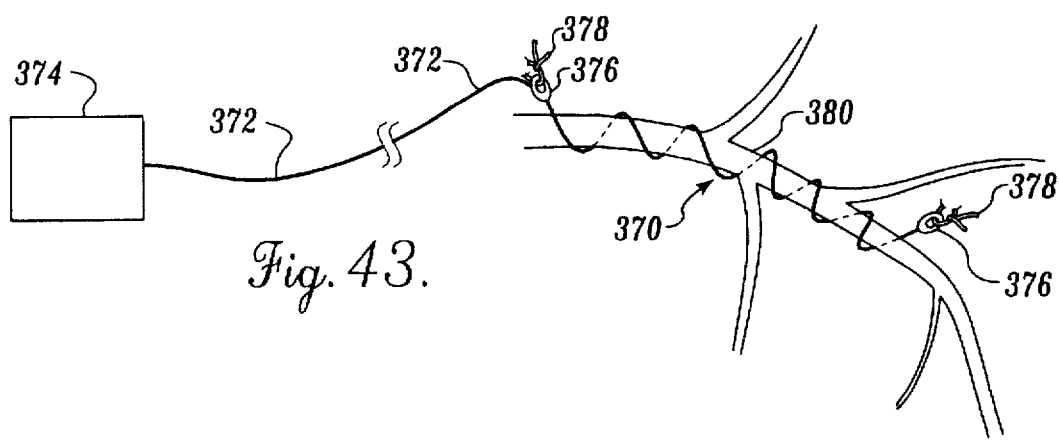
Figure 44:
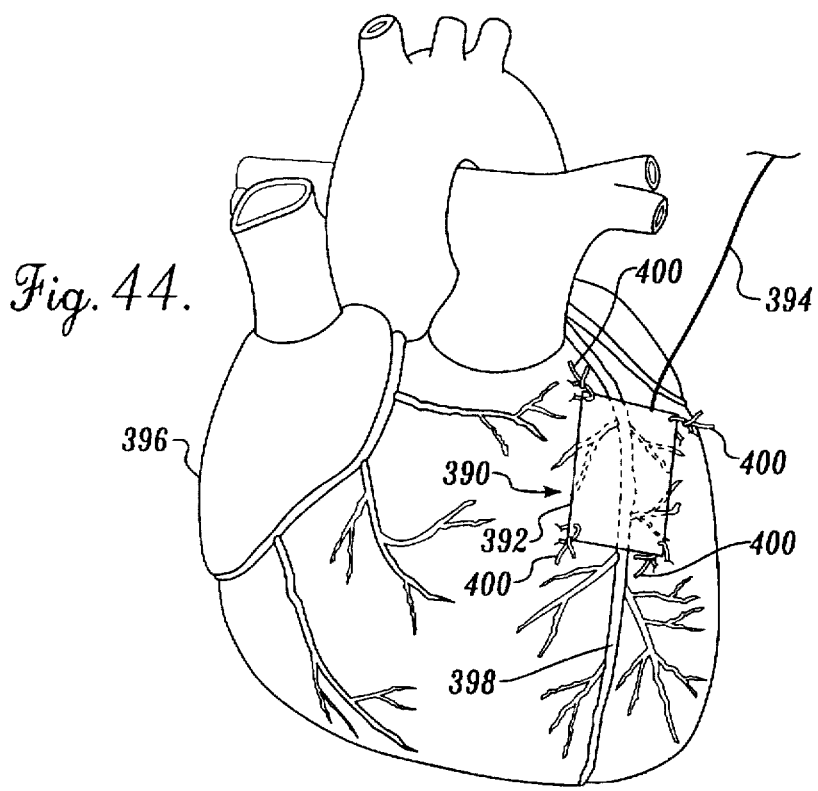
Figure 45:
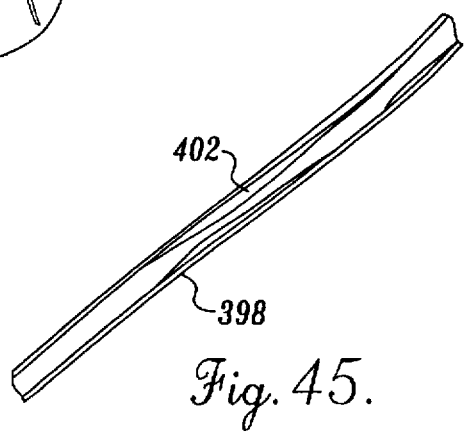
Figure 46:
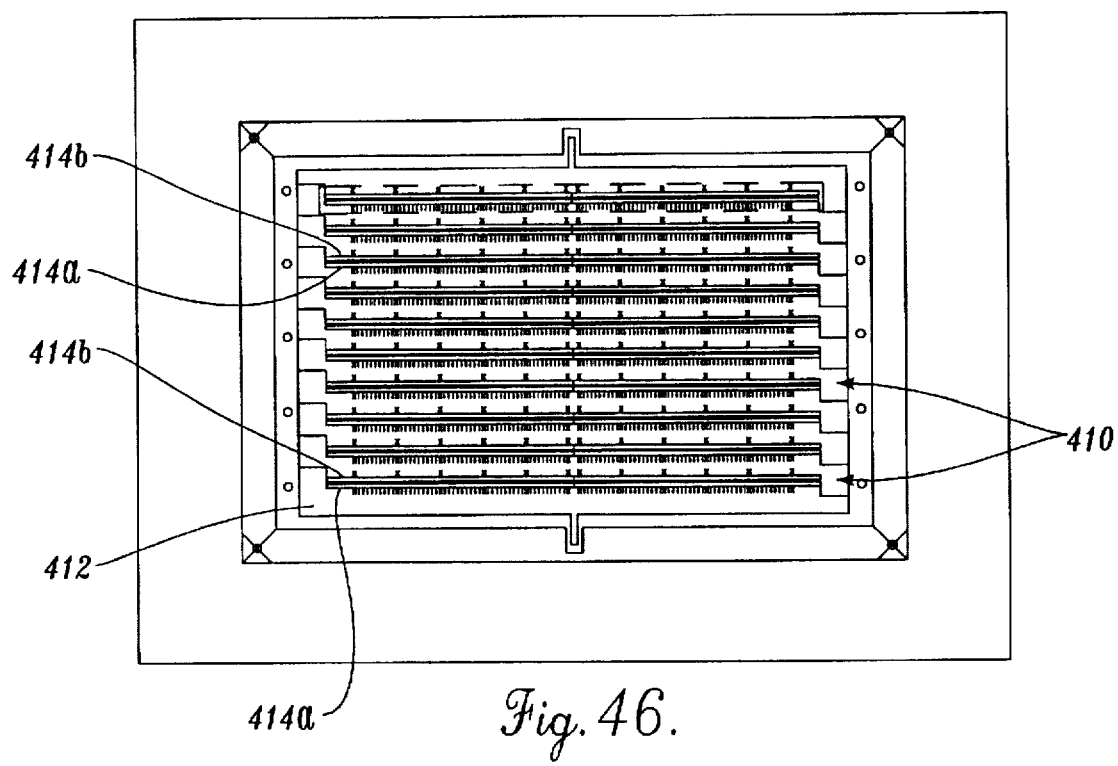
Figure 47:
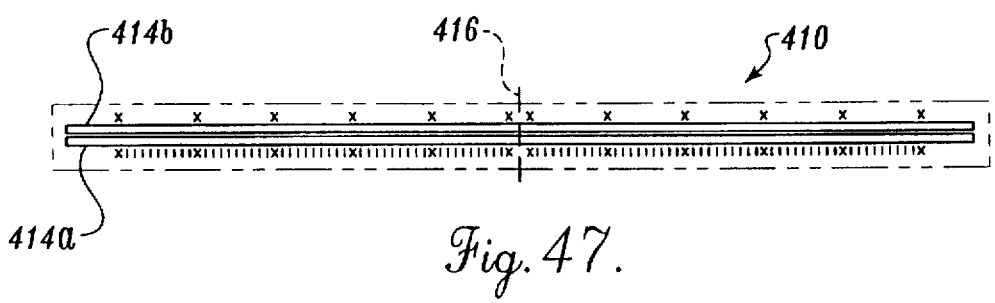
Figure 48:
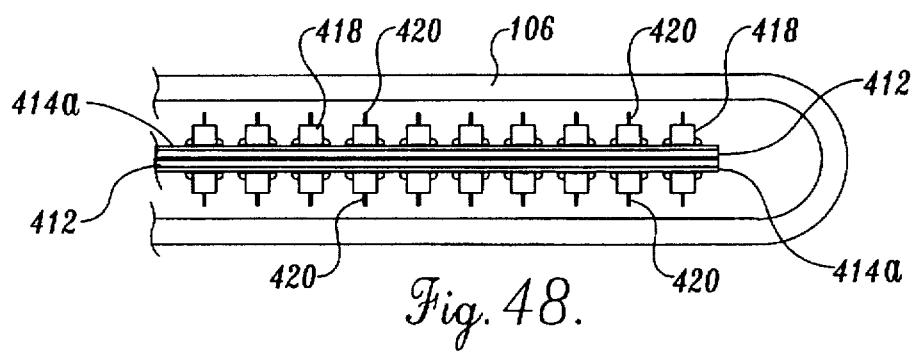
Figure 49:
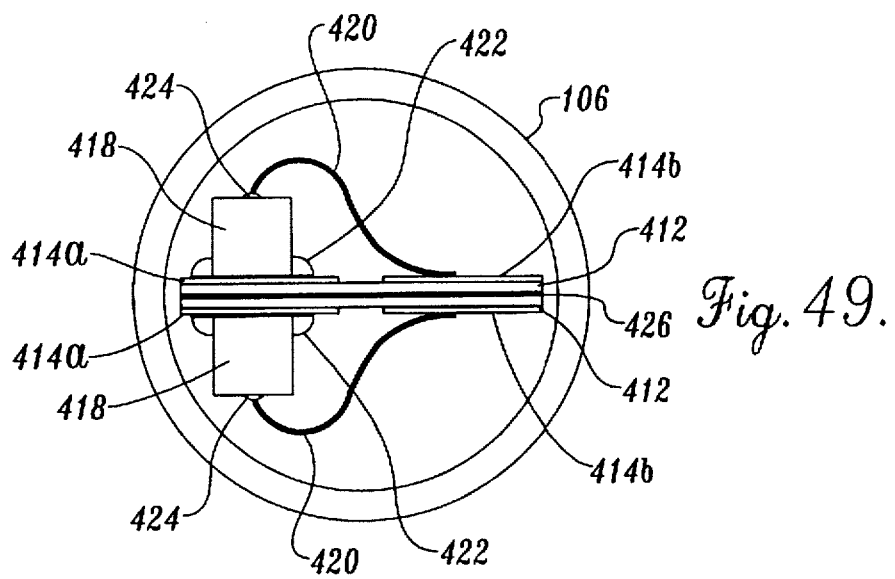
Figure 50:
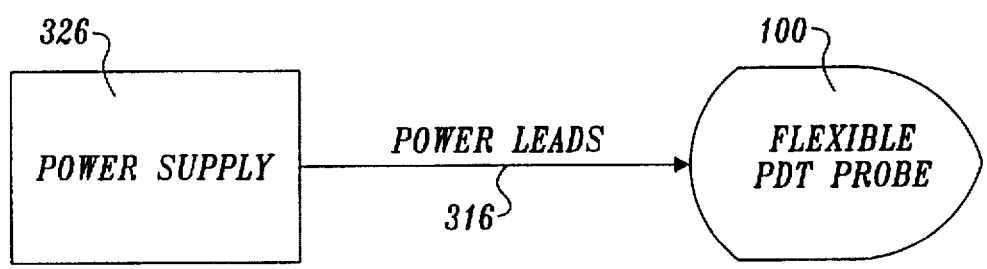
Figure 51:
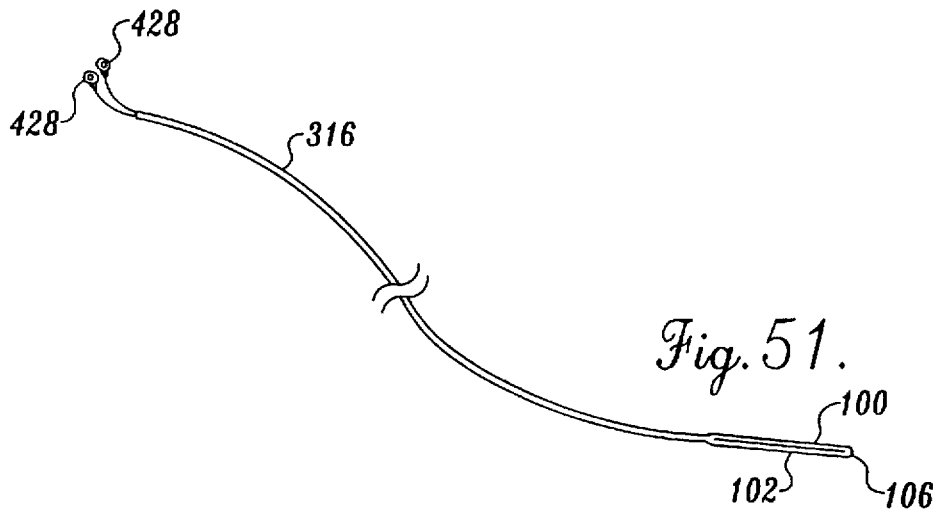
Figure 52:
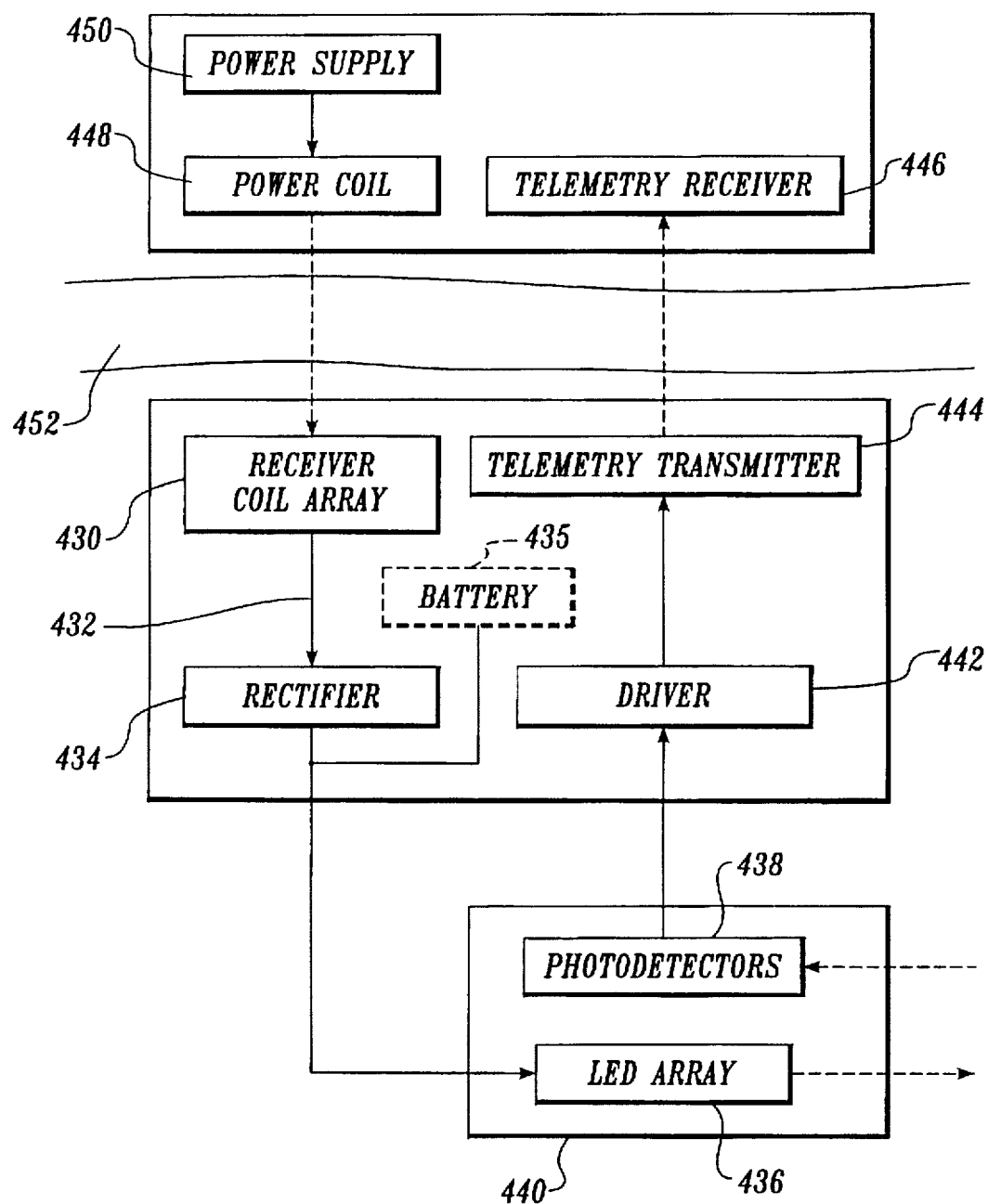
Figure 53:
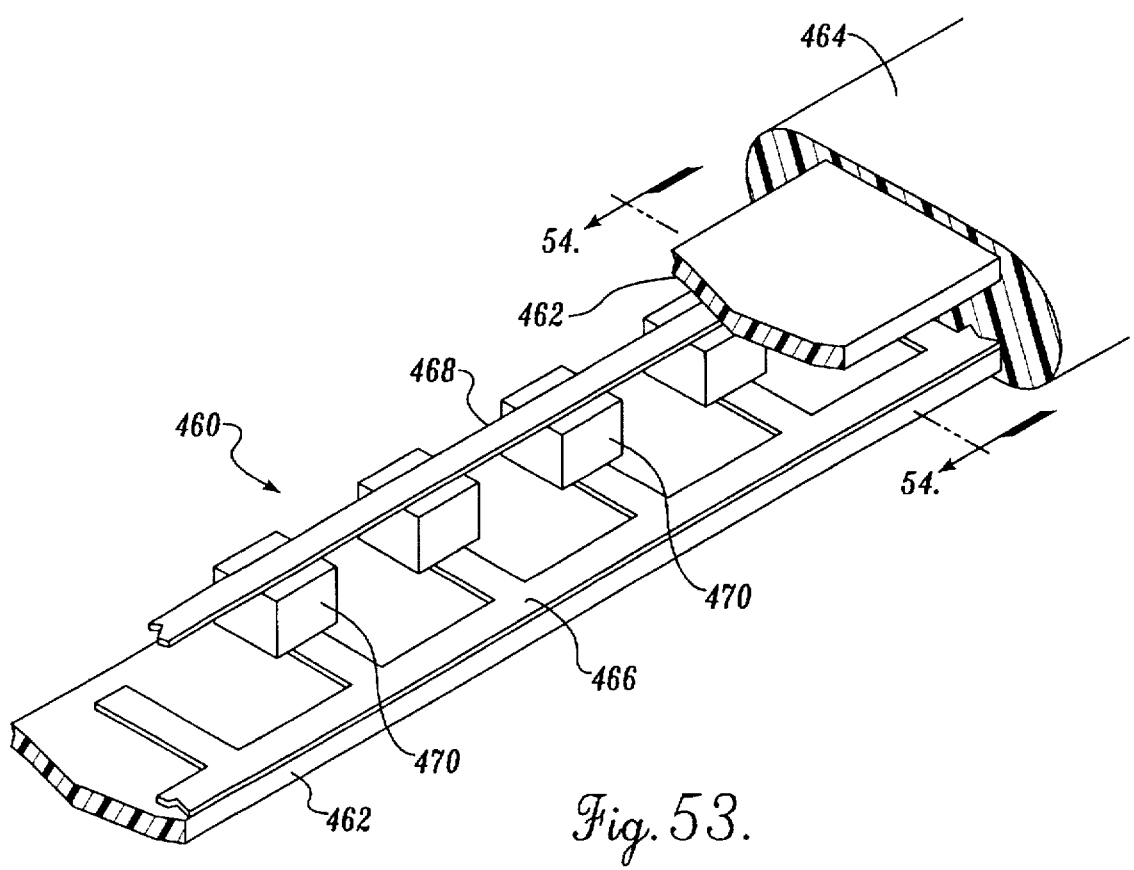
Figure 54:
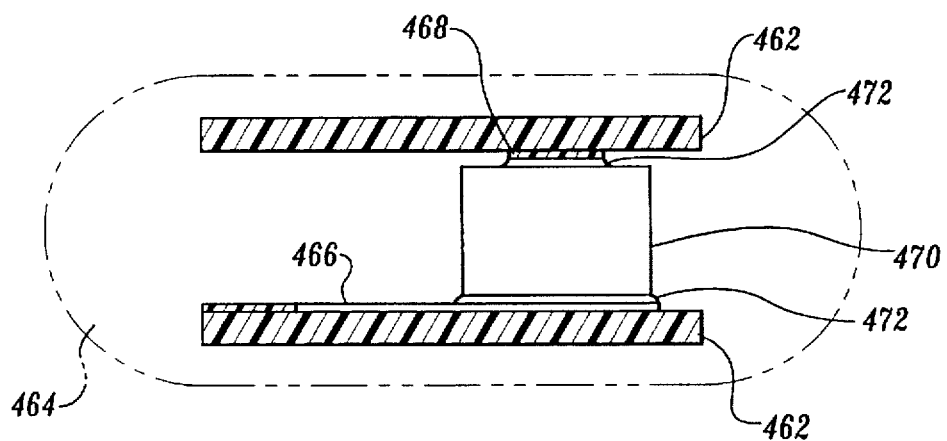
Figure 55:
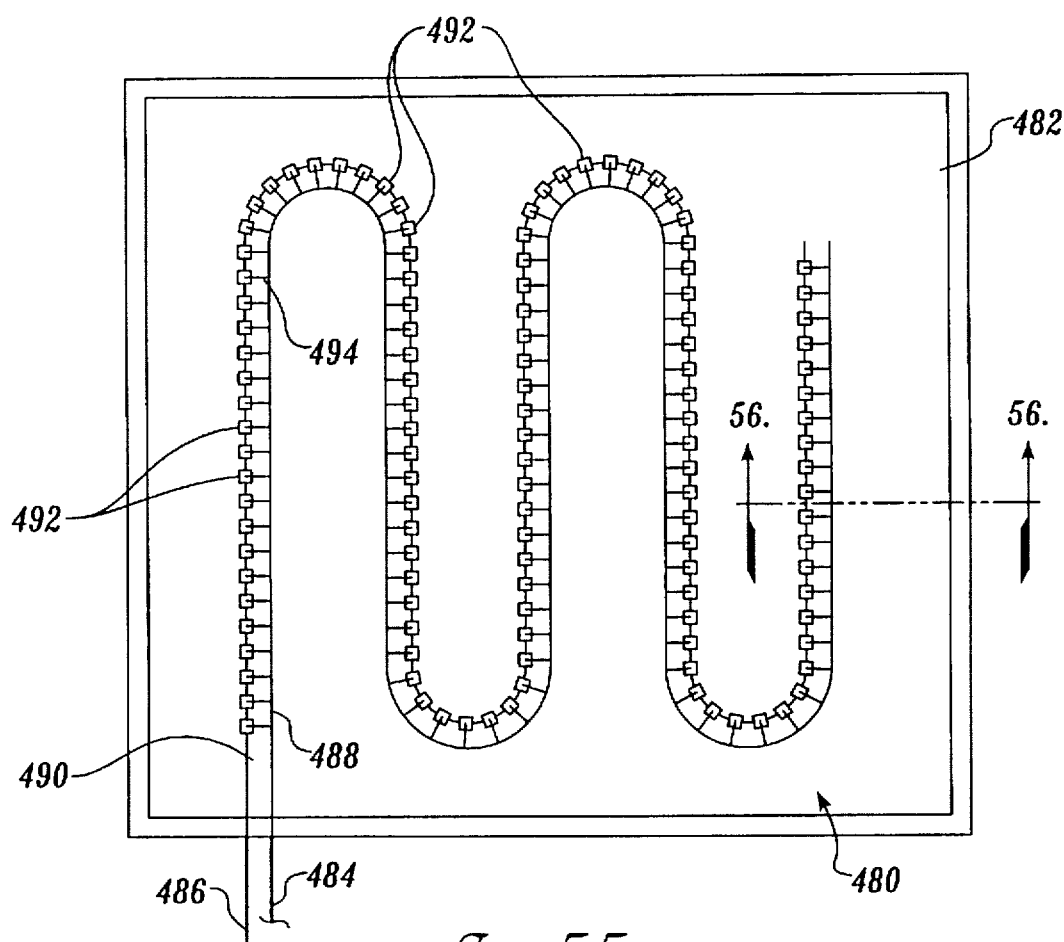
Figure 56:
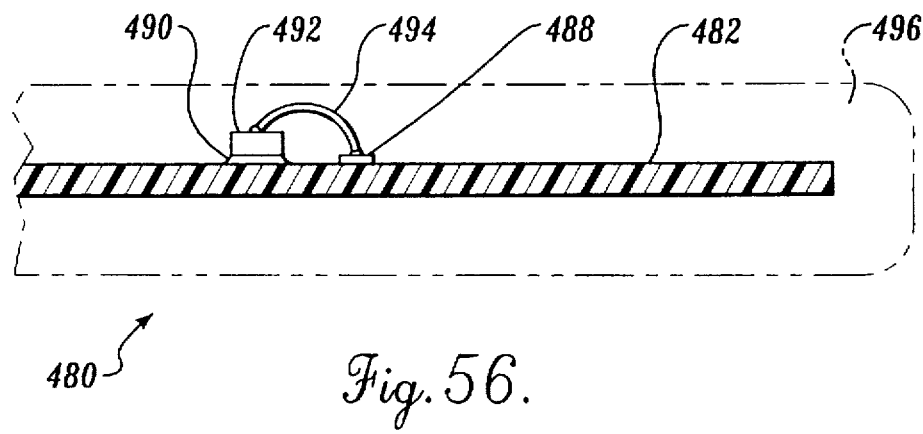
Figure 60:
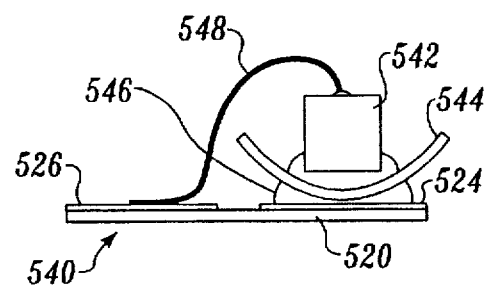
Figure 61:
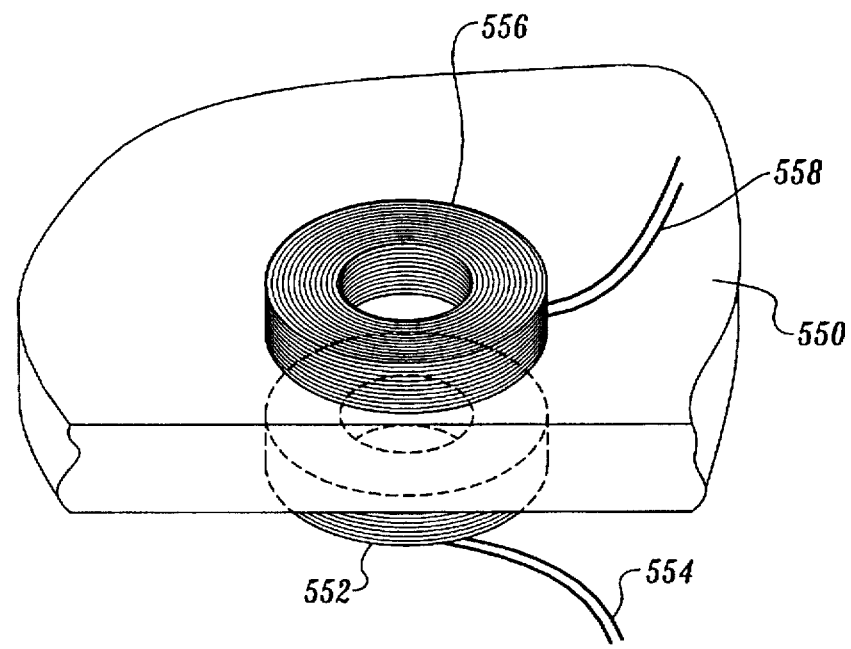
Figure 62:
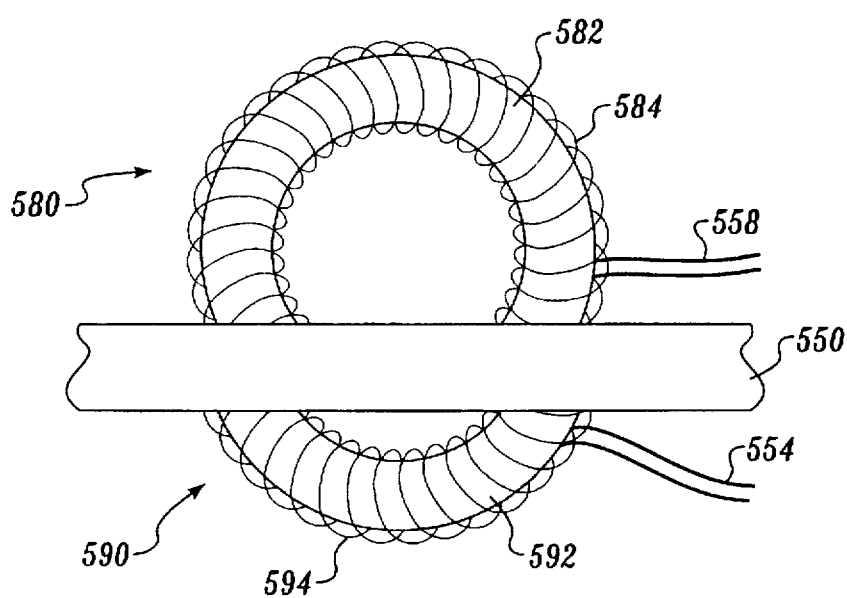
Figure 63:
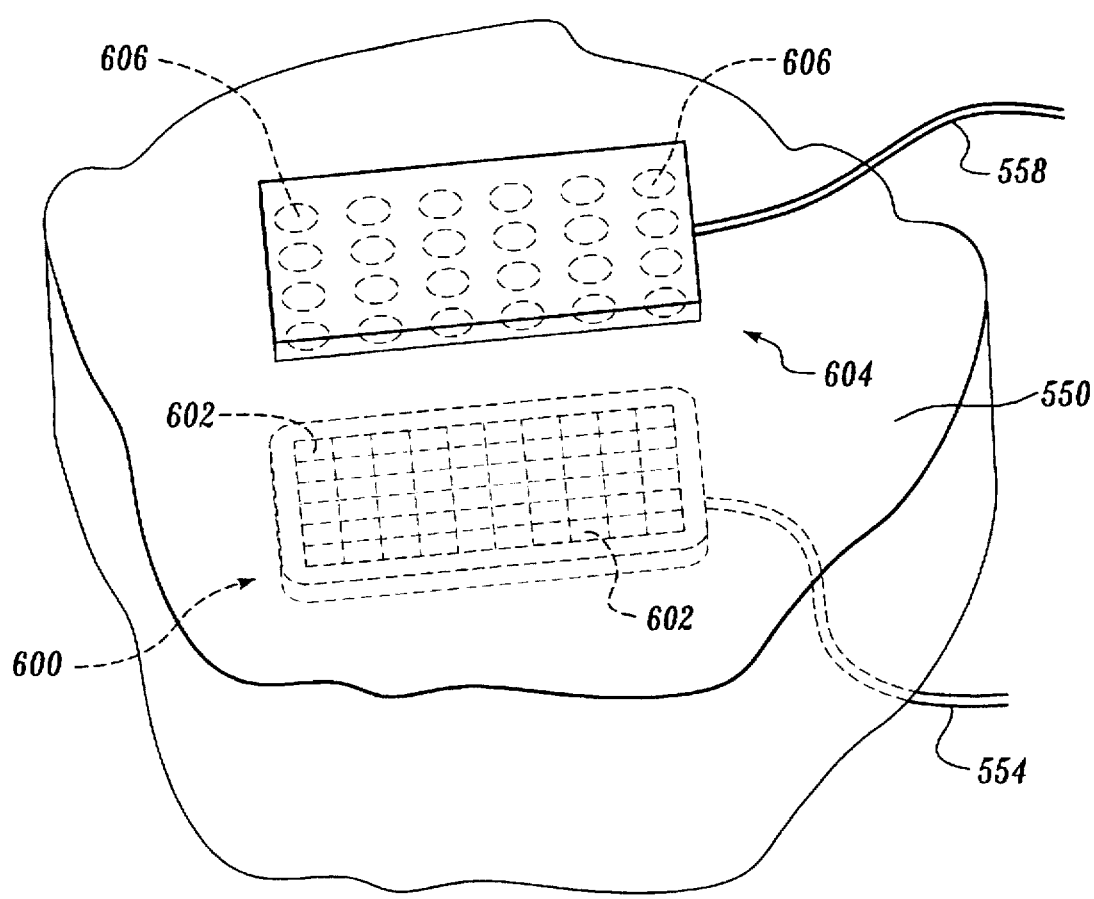

7 balloon cuff, with lumens and leads extending through an opening in the patient's skin;

FIG. 34 is an isometric view of the fifth embodiment of the flexible probe;

FIG. 35 is a side view of the fifth embodiment of the flexible probe;

FIG. 36 is a sectional view showing a flexible probe threaded through a nasal passage and into the entrance of a patient's stomach;

FIG. 37 is sectional view of a portion of the esophagus in which the flexible probe has been threaded;

FIG. 38 is a sectional view showing a flexible probe having electrical lines attached to one end and a suspension lead attached to the other end and extending through the esophagus and out through the nasal passage of a patient;

FIG. 39 is a sectional view of a portion of the esophagus in which the flexible probe of FIG. 38 is disposed;

FIG. 40 is a side view of a sixth embodiment of the flexible probe in which a soft tip is temporarily attached to a distal end of the probe so that peristalsis advances the probe into the bowel;

FIG. 41 is a sectional view of the bowel, showing the flexible probe sutured in place and a proximal end of an attached lead passing through an gastrostomy site in the stomach and out through the abdominal wall;

FIG. 42 is a sectional view of a bowel, showing the flexible probe sutured at a treatment site inside the bowel and leads extending outside the abdominal cavity through a stoma site;

FIG. 43 is a side view of a branching artery, showing a seventh embodiment of the flexible probe coiled about the artery;

FIG. 44 is an isometric view of a heart showing the fourth embodiment of the flexible probe overlying a cardiac vessel;

FIG. 45 is a sectional view of a cardiac vessel showing arteriosclerosis plaque built up on the interior surface;

FIG. 46 is a plan view of a flexible substrate upon which a plurality of LEDs can be mounted to produce a plurality of flexible probe circuits;

FIG. 47 is a plan view of a single flexible substrate probe substrate and conductive strips for mounting a plurality of LEDs;

FIG. 48 is an enlarged side view of a distal end of a flexible probe in which a plurality of LEDs are mounted on opposite sides of flexible substrates;

FIG. 49 is a cross-sectional view of the flexible probe shown in FIG. 48;

FIG. 50 is a block diagram of a system for administering PDT using the flexible probe;

FIG. 51 is a plan view of the PDT flexible probe;

FIG. 52 is a block diagram showing the components of a PDT system that uses a flexible probe;

FIG. 53 is a greatly enlarged cut-away view of an embodiment of a flexible probe in which light sources are mounted between two facing flexible substrates;

FIG. 54 is a cross-sectional view of the embodiment shown in FIG. 53;

FIG. 55 is a plan view of another embodiment of a flexible probe formed as a sheet, for administering PDT;

FIG. 56 is a cross-sectional view of the embodiment of FIG. 55, taken along section lines 56—56;

FIG. 57 is an isometric view of a portion of an embodiment in which LEDs having two characteristic wavelengths are mounted between conductive traces on a flexible substrate, with the polarities of the LEDs having one characteristic wavelength reversed relative to those having the other characteristic wavelength;

FIG. 58 is a cross-sectional elevational view of the embodiment of the flexible probe shown in FIG. 57;

FIG. 59 is a plan view of a planar array of LEDs mounted on a flexible substrate that is encapsulated in a transparent material;

FIG. 60 is a sectional view of a pair of conductive traces on which an LED is mounted on a reflector;

FIG. 61 is an isometric view of power transmitter and receiver coils disposed on opposite sides of a cutaneous layer;

FIG. 62 is an alternative embodiment of power transmitter and receiver coils disposed on opposite sides of a cutaneous layer; and FIG. 63 illustrates an infrared source and receiver disposed on opposite side of a cutaneous layer, for transmitting power for the flexible probe.

DESCRIPTION OF THE PREFERRED EMBODIMENT

Elongate Flexible Probes

Figure 1:
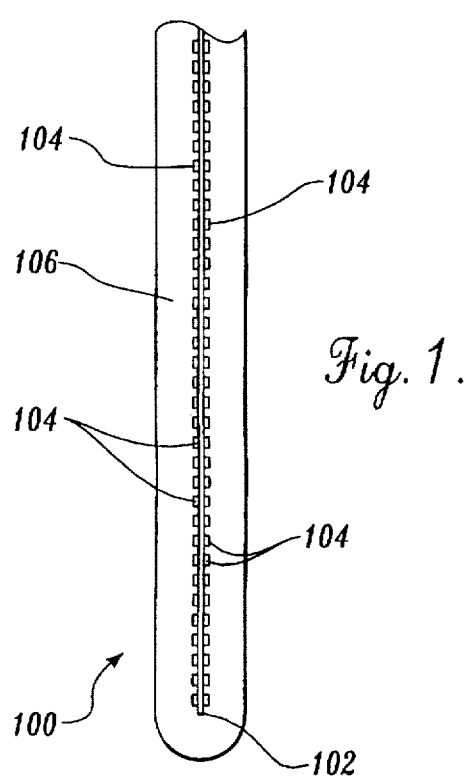
FIG. 1 is a greatly enlarged side view of a distal portion of a first embodiment of a flexible probe in accord with the present invention.

A first embodiment of a flexible probe 100 in accordance with the present invention is illustrated in FIG. 1. Flexible probe 100 is elongate in shape and comprises a flexible substrate 102 comprising a polymer material that readily bends without breakage. In an initial prototype of the flexible probe, the polymer material used is approximately 0.002" thick and comprises Kapton™ polyimide film, which is sold by E. I. DuPont De Nemours & Co. Other types of polymers and thinner material can be used for the flexible substrate in each of the embodiments of the present invention that are described below. The flexible substrate comprising flexible probe 100 (and the other embodiments described below) is sufficiently flexible and strong to enable it to be folded back on itself (through an angle of about 180°) along a line, rolled, twisted, and otherwise distorted, without any damage to the substrate or to conductive traces (discussed below in regard to FIG. 46) that are applied to the flexible substrate.

Although not shown in FIG. 1, a plurality of conductive traces are applied to flexible substrate 102 to convey an electrical current to energize a plurality of light emitting sources 104 that are mounted on and supported by the flexible substrate. In connection with this invention, it is also contemplated that other types of electronic microcircuits may be mounted on the flexible substrate instead of, or in addition to, light emitting sources 104. Such electronic microcircuits may include ultrasonic transmitters and emitters, sensors such as photodetectors, and other electronic circuitry for use in effecting either a medical treatment or a diagnostic function using the flexible probe within a patient's body. It should be noted that the present invention is not limited for use with human patients, but may also be used, for example, by veterinarians to treat and/or diagnose medical problems in pets, livestock and other animals. For use in administering light during PDT, flexible substrate 102 and light emitting sources 104 are enclosed in a clear (light transparent) biocompatible polymer envelope 106. In this and other of the embodiments intended for use in providing PDT, the light emitting sources preferably comprise LEDs; however, it is also contemplated that other types of light emitting electronic circuits, such as laser diodes or a thin film electroluminescent panel can alternatively be fabricated on the flexible substrate for use in administering the PDT. For example, thin film electroluminescent display panels using ZnS:Mn phosphors are well known in the prior art and the flexible substrate is equally applicable as a support for a plurality of conductive traces, between which are sandwiched the light-emitting phosphor layers.

Figure 2:
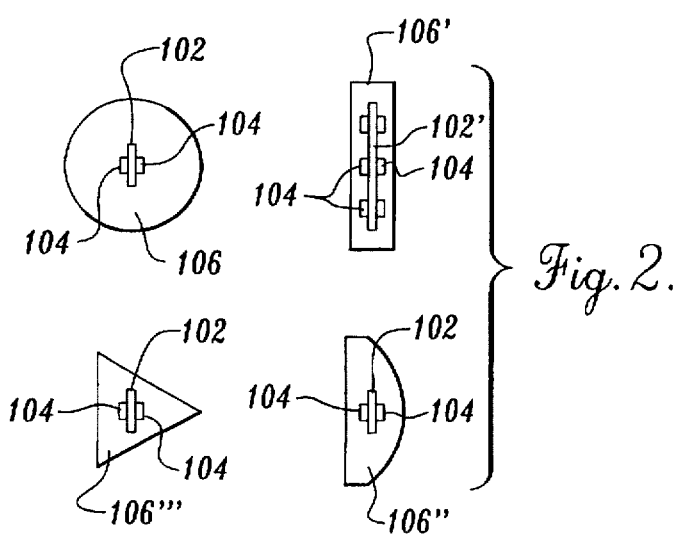
FIG. 2 shows cross-sectional views of four different profiles of the flexible probe.

FIG. 2 illustrates various other cross-sectional shapes for the envelope provided for the flexible probe. These shapes include an envelope 106' that has a rectangular cross section and encloses a flexible substrate 102', which is sufficiently broad to enable a plurality of light emitting sources 104 to be mounted across its width. Also illustrated are an envelope 106", which has a generally half-round cross-sectional shape, and an envelope 106'" an equilateral triangle cross-sectional shape. The various cross-sectional shapes illustrated for the envelope in FIG. 2 are merely exemplary of various cross-sectional shapes contemplated for use with flexible probes made in accordance with the present invention.

No attempt is made in this disclosure to teach optimum exposure times and light intensities for conducting PDT using the present invention. Planned clinical trials will help to determine such variables for various types of abnormal tissue and in regard to patient specific variables. The basis premises of PDT are well known to those of ordinary skill in this art and need not be recited to fully disclose the present invention. For example, a variety of photoreactive agents are known, as evident from references such as "Photosensitizing Activity of Water and Lipid-Soluble Phthalocyanines on *Escherichia coli,*" Bertoloni et al., "photodynamic Effects of Dyes on Bacteria," Webb et al., "Phototoxicity of Quinoline Methanols and Other Drugs," Ison et al., "Research Progress in Organic-Biological and Medicinal Chemistry," Ballio et al., "Photodynamic Therapy with Endogenous Protoporphyrin," Kennedy et al., and "Immunophototherapy for the Treatment of Cancer of the Larynx," Schlager et al. It is contemplated that conventional photoreactive agents of the types discussed in the preceding references can be very effective in implementing PDT using the present invention. Eventually, it is likely that even more effective photoreactive agents will be identified for use in extended term PDT, which the present invention is well suited to provide.

Figure 3:
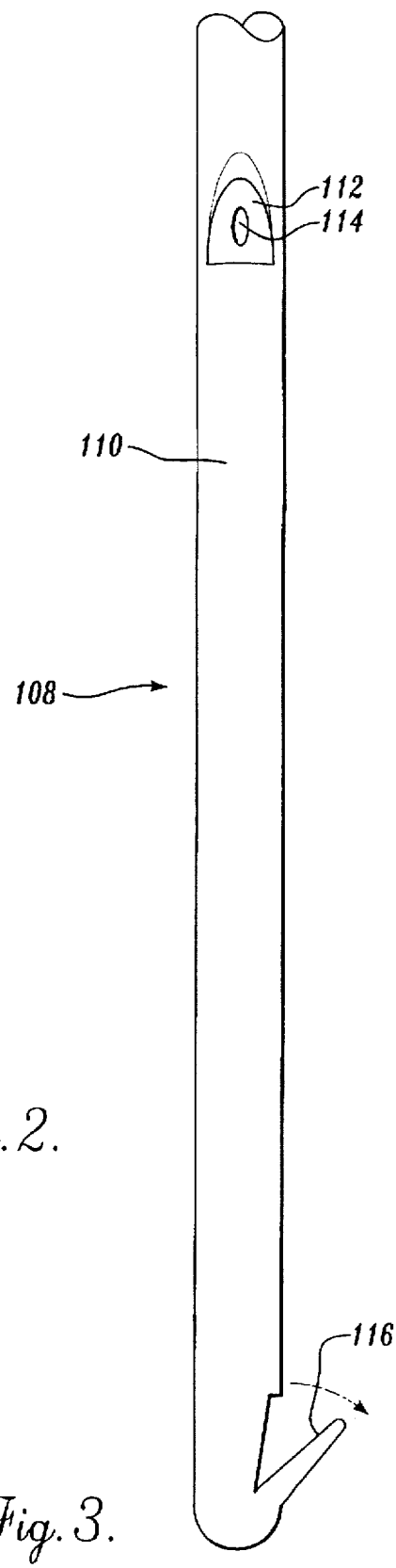
FIG. 3 is a greatly enlarged side view of a distal portion of a second embodiment of the flexible probe.

In FIG. 3, a second embodiment of a flexible probe 108 is illustrated. Flexible probe 108 differs from the first embodiment by including a flexible envelope 110 on which is formed a loop 112. Loop 112 includes an orifice 114, which as shown below, provides an attachment point for temporarily mounting flexible probe 108 in a fixed position at a treatment site inside a patient's body. Flexible probe 108 also includes a barb 116 disposed at its distal end. Barb 116 is formed of the polymer material comprising envelope 110 and has a characteristic elasticity that causes the barb to flex to an open position in which it extends outwardly from the longitudinal axis of the flexible probe, as shown in FIG. 3. However, because it is flexible, barb 116 can readily be closed to minimize the cross-sectional area of flexible probe 108 at its distal end.

Figure 4:
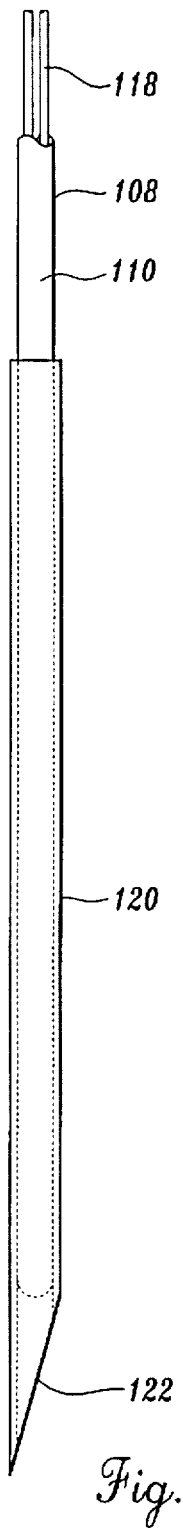
FIG. 4 is side elevational view of a straight guide tube through which the flexible probe is delivered to an internal treatment site, showing the flexible probe being guided through a lumen of the guide tube.

As explained below, flexible probes made in accordance with the present invention can be placed at a treatment site within a patient's body in ways that benefit from the flexibility of the flexible probe and its ability to bend or fold. In FIG. 4, a guide tube 120 is illustrated having a pointed end 122 for piercing a cutaneous layer (or other tissue layer) of a patient's body (not shown) or for piercing the outer surface of an internal organ in which is disposed a treatment site to which the flexible probe is to be advanced and left in place.

Figure 5:
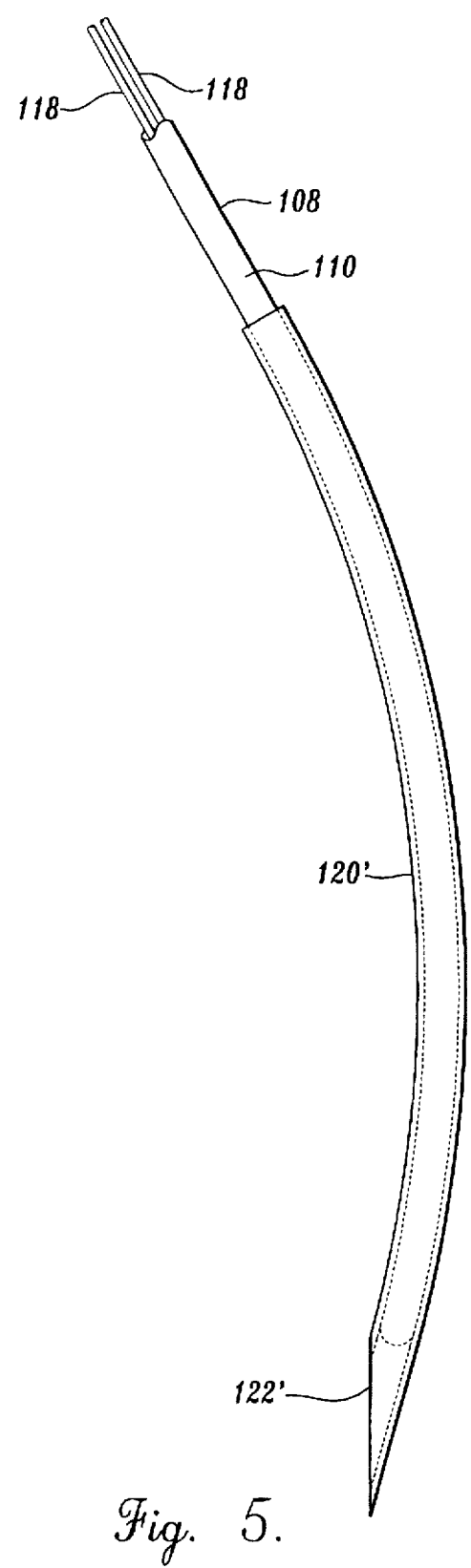
FIG. 5 is a side elevational view of a curved guide tube through which the flexible probe is delivered to an internal treatment site, showing the flexible probe being guided through a lumen of the guide tube.

In FIG. 5, a guide tube 120' is illustrated that has a predefined radius of curvature and a distal end terminating in a sharp point 122' for piercing the cutaneous layer or outer surface of an organ to facilitate placement of flexible probe 108. Due to the characteristic flexibility of flexible probe 108, it is easily advanced around the radius of curvature of guide tube 120' for insertion and disposition at the treatment site within the patient's body. Electrical power and/or signals to and from the circuitry comprising the flexible probe are conveyed through leads 118, which extend either outside the patient's body or to a site remote from the treatment site where power and/or signals pass through the cutaneous layer of the patient's body. Details of such an arrangement are discussed below.

Figure 6A:
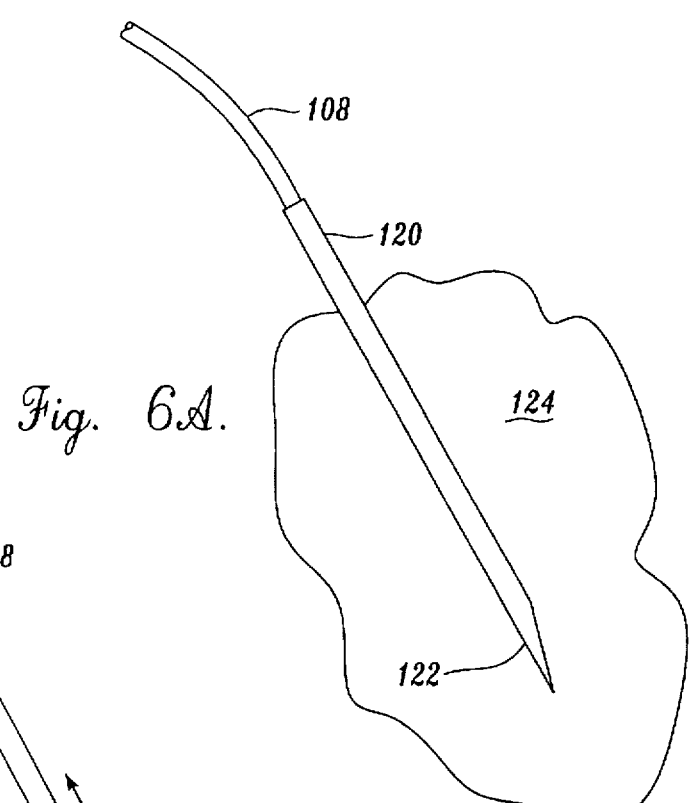
FIG. 6A is a side view of the straight guide tube of FIG. 4, showing the guide tube used to deliver the second embodiment of the flexible probe to a treatment site inside a tumor or other type of tissue mass.
Figure 6B:
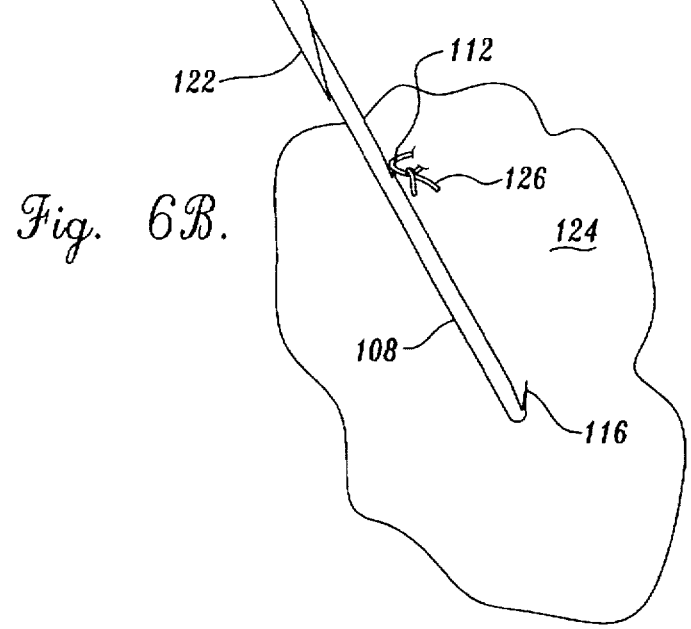
FIG. 6B is a side view of the straight guide tube, showing it being drawn back from the treatment site over an electrical lead that is coupled to the second embodiment of the flexible probe.

FIGS. 6A and 6B illustrate the steps involved in disposing flexible probe 108 at a treatment site within a tumor 124. Sharpened end 122 of guide tube 120 is inserted into tumor 124 to an appropriate depth, e.g., just past the center of the tumor. Flexible probe 108 is either contained within guide tube 120 during its insertion, or is subsequently inserted into the tumor through the inner passage of guide tube 120 after the guide tube has been positioned within tumor 124. Thereafter, guide tube 120 is withdrawn over the leads extending to flexible probe 108, as the flexible probe is held in place. Barb 116 flexes outwardly as the distal end of the flexible probe extends from the distal end of the guide tube. The barb engages tissue inside tumor 124, preventing flexible probe 108 being pulled from inside tumor 124 as the guide tube is withdrawn. Optionally, a suture 126 may be used to secure loop 112 on flexible probe 108 to tumor 124 (or to another adjacent soft tissue structure). Guide tube 120 is withdrawn from the patient's body, and leads 118 are coupled to a power source and/or other instrumentation to activate the electronic circuits on the flexible probe.

An alternative embodiment of a flexible probe 130 is shown in FIG. 7, following its insertion into tumor 124. Flexible probe 130 includes two loops 112 that extend outwardly from opposite sides of the flexible envelope. As shown in FIG. 7, loops 112 are secured by sutures 131 to adjacent tissue 128 to retain flexible probe 130 fixed within tumor 124.

Another technique for inserting a flexible probe into tumor 124 (or into another type of tissue mass) employs a peel-away sheath 132, which is well known to those of ordinary skill in the art. Peel-away sheath 132 is shown in FIGS. 8–13, which illustrate its configuration and its use in placing flexible probe 108 at a treatment site within tumor 124. As shown in FIG. 9, peel-away sheath 132 is shaped as an annular cylinder having frangible seams 134 disposed on opposite sides of the cylindrical sheath, extending longitudinally along its length. A lancet 138 having a sharpened point 122 is inserted inside a bore 136 of peel-away sheath 132, so that the sharpened point extends beyond the distal end of the sheath, and the assembly is inserted within tumor 124, as shown in FIG. 10. Sharpened end 122 enables the assembly to readily pierce through a cutaneous layer or other tissue surface and enables the assembly to be readily advanced into tumor 124 (or into other types of tissue mass).

Figure 11:
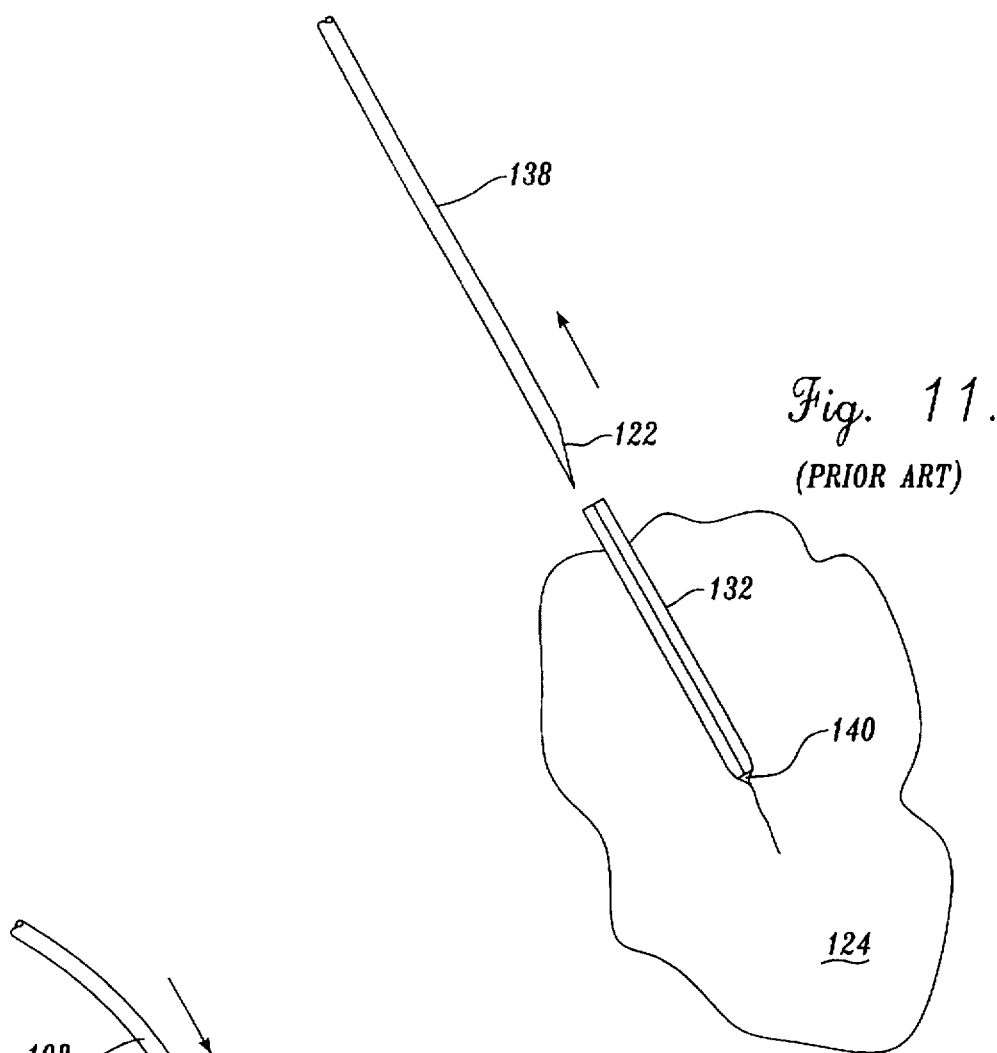
FIG. 11 is a side view showing the prior art lancet being withdrawn from the peel-away sheath of FIG. 8.
Figure 12:
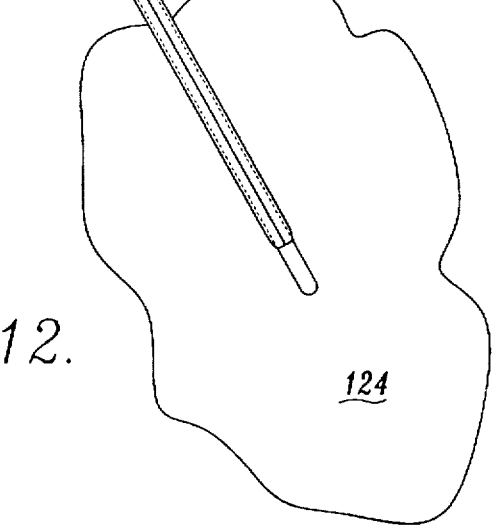
FIG. 12 is a side view showing the flexible probe being positioned in the tissue mass through the peel-away sheath of FIG. 8.
Figure 13:
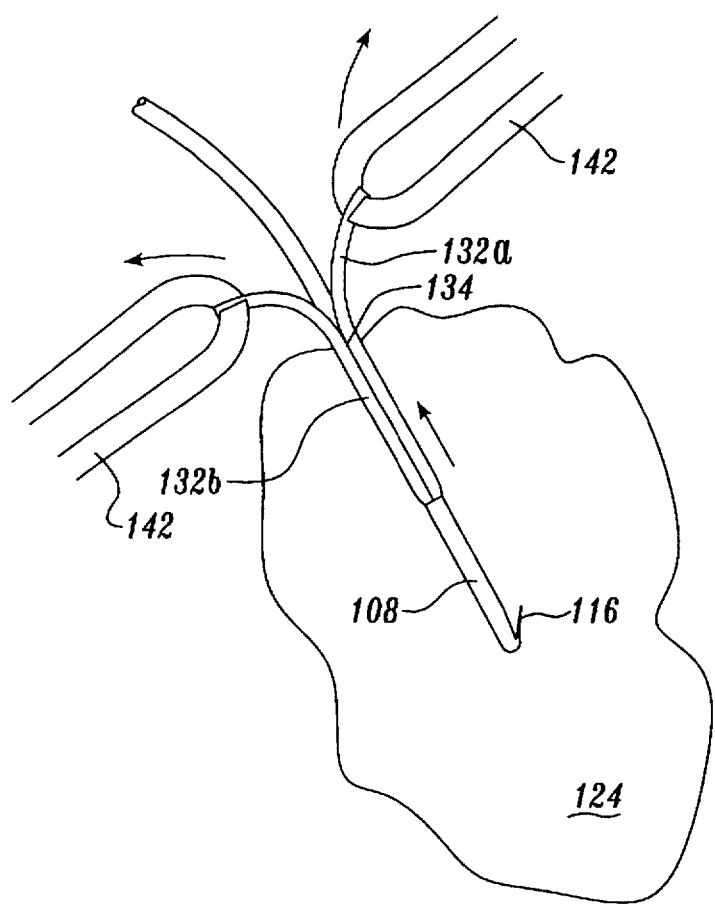
FIG. 13 is a side view illustrating how the peel-away sheath is removed from the second embodiment of the flexible probe by splitting the guide tube longitudinally while withdrawing it from the tissue mass.

In FIG. 11, lancet 138 is withdrawn from peel-away sheath 132, which remains temporarily fixed within a passage 140 in the tumor, produced by insertion of the assembly. Then, as shown in FIG. 12, flexible probe 108 is inserted through the bore of peel-away sheath 132 and into passage 140 so that the flexible probe extends beyond the distal end of the peel-away sheath and inside tumor 124. The flexibility of the flexible probe facilitates threading it to the point in the patient's body where it can be inserted in the bore of the sheath. To reach this point, it may be necessary to pass the flexible probe through a body lumen or along a curved path within the body. Finally, as shown in FIG. 13, sides 132a and 132b of the peel-away sheath are split apart from each other along frangible seams 134 using forceps (endoscopic or conventional) 142. The forceps simultaneously split the frangible seam and withdraw sides 132a and 132b from inside tumor 124. Flexible probe 108 is held in place within tumor 124 by barb 116, which engages tissue in the interior of the tumor.

Figure 14:
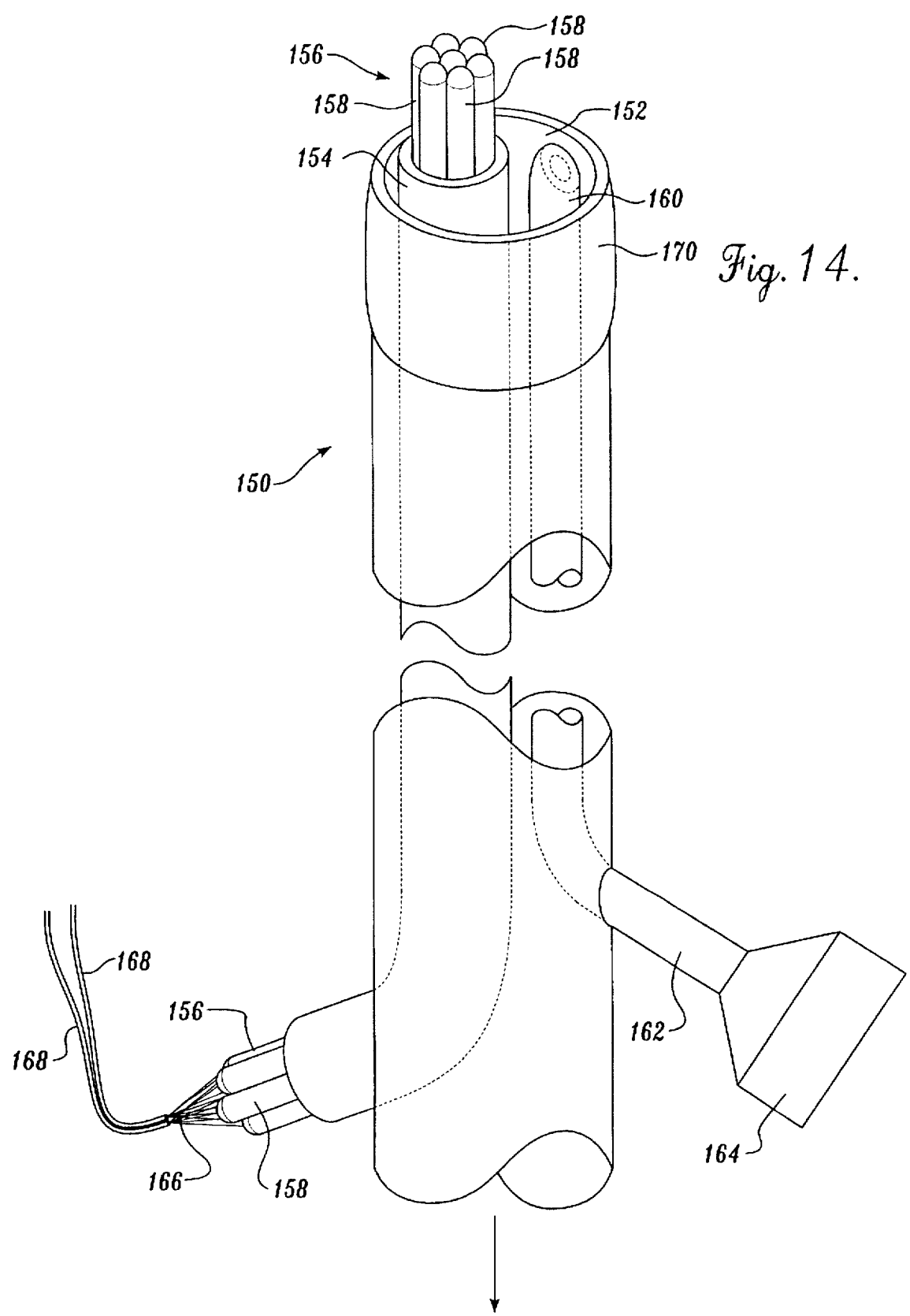
FIG. 14 is an isometric cut-away view of a third embodiment of the present invention and a catheter for inserting a plurality of flexible probes through a body passage to a treatment site within a patient's body.
Figure 15:
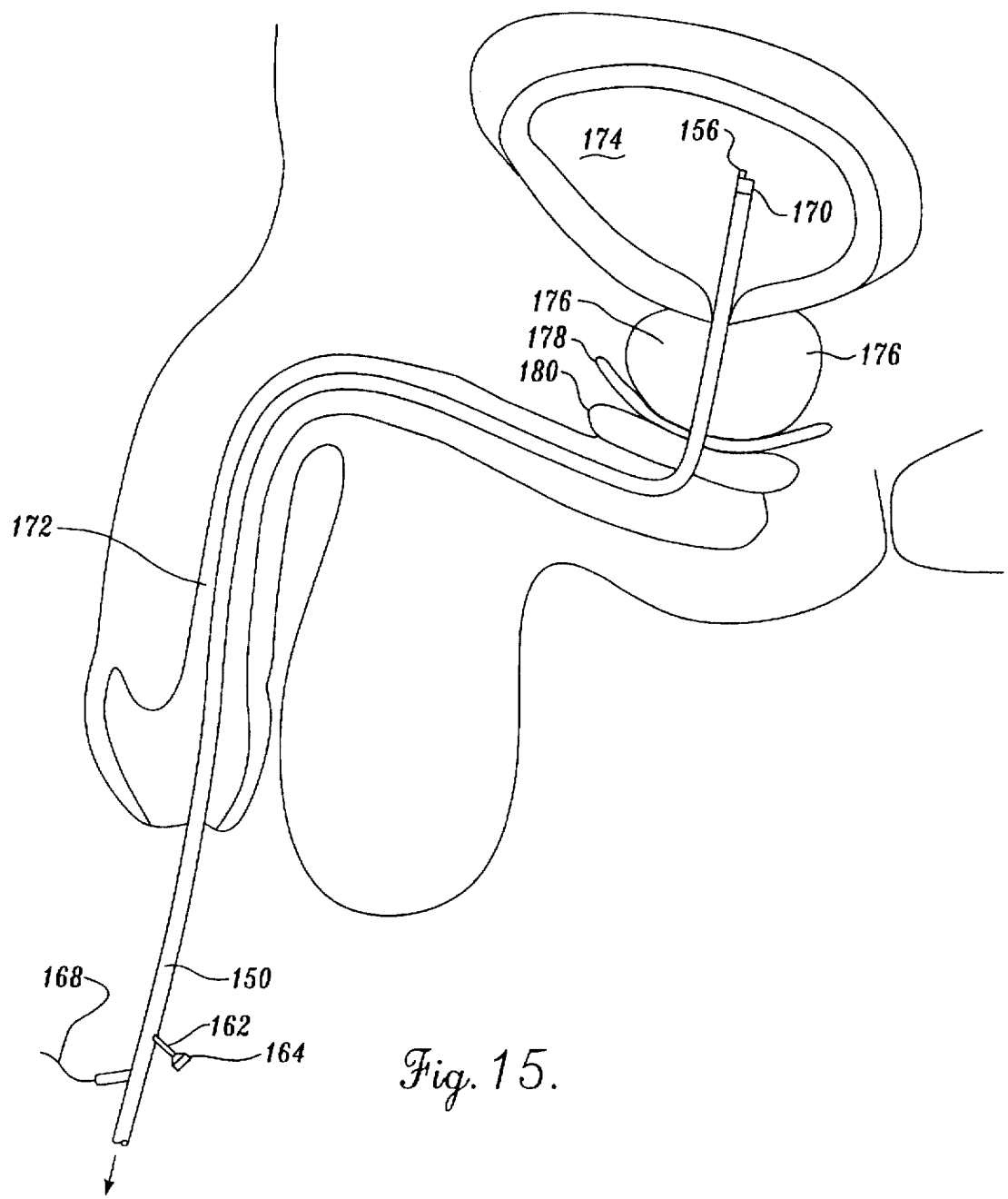
FIG. 15 is a sectional view of a penis, showing the third embodiment in a catheter that is inserted into a bladder through a urethra passage.
Figure 29:
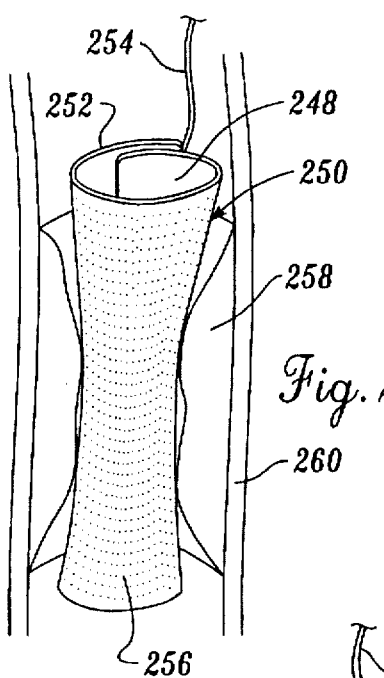
FIG. 29 is a sectional view of an internal passage in a patient's body in which the rolled flexible probe has been inserted.

Since a flexible probe made in accordance with the present invention can readily bend, it is easily threaded into a treatment site within a patient's body, through an internal body or organ lumen. An example in which the present invention is used to apply PDT inside a male patient's bladder is illustrated in FIGS. 14–16 (A–D). In FIG. 14, a urinary catheter 150 is illustrated that includes a central lumen 152. Within central lumen 152 is disposed a guide lumen 154, which exits urinary catheter 150 adjacent a proximal end of the urinary catheter. Guide lumen 154 guides a bundle 156 of flexible probes 158 that are inserted into the guide lumen from its proximal end and extend just past the distal end of urinary catheter 150. Also disposed within lumen 152 is a balloon inflation lumen 160, having a distal end in fluid communication with a balloon 170 that is disposed at the distal end of urinary catheter 150. Inflation lumen 160 is also in fluid communication with an external line 162, to which it is attached adjacent the proximal end of the urinary catheter. External line 162 terminates in a connector 164 that is suitable for connecting to a source of compressed air (or other type of fluid under pressure) used to inflate balloon 170. Balloon 170 extends annularly around the outer perimeter of the distal end of urinary catheter 150, but is not inflated until after the distal end of the urinary catheter and balloon 170 have been inserted into the patient's bladder. Extending from the distal ends of each of the flexible probes 158 comprising bundle 156 are electrical lines 166, which are combined in leads 168. Leads 168 are connected to a source of electrical current and to instrumentation appropriate to process signals conveyed from the flexible probes.

A portion of lumen 152 remains open along the entire length of urinary catheter 150, enabling urine to pass freely through lumen 152 to an external receptacle (not shown). As illustrated in FIG. 15, urinary catheter 150 is threaded through a urethra 172, past a pubic bone 180, seminal glands 178, and prostate gland 176 into a patient's bladder 174. Balloon 170 is then inflated with pressurized air or other pressurized fluid and the urinary catheter is drawn back through urethra 172 so that balloon 170 seats within the opening into bladder 174, forming a sealing cuff. As urinary catheter 150 is drawn backwards along bundle 156, flexible probes 158 splay outwardly apart from each other, within the interior of bladder 174. Although not shown in FIG. 16A, light sources within each of flexible probes 158 are energized to provide PDT therapy to the interior surface of bladder 174 for treatment of tumors and other medical disorders that are appropriately treated using PDT.

FIGS. 16B–16D illustrate a flexible probe 182 in which the distal end of the flexible probe is turned back toward itself in a loop and adhesively attached at a point 186, as shown in FIG. 16C. The loop is sufficiently flexible to be collapsed, but its inherent elasticity causes it to spring into an open loop when not restrained. Inside flexible probe 182 is provided a flexible substrate 184 on which a plurality of light sources (not visible in the drawing figures) are mounted. As illustrated in FIG. 16B, use of flexible probes 182 in urinary catheter 150 to provide PDT inside a hollow organ, such as bladder 174, increases the total area of the flexible probe from which light is emitted and decreases any risk of perforating the organ wall with the tip of the flexible probe. When urinary catheter 150 is withdrawn from the bundle of flexible probes 182, the probes not only splay outwardly from each other, but also each form an open loop to increase the total area from which light is emitted from the flexible probes.

Flexible Sheet Probes

In FIGS. 17–21, use of a flexible sheet probe 190 is illustrated in accordance with the present invention. Flexible sheet probe 190 includes a generally quadrilateral shaped flexible substrate 196. This embodiment comprises a flexible substrate sheet that is substantially wider and longer than it is thick. It is contemplated that the flexible sheet probe can be made in any of a variety of different shapes, such as "T-shaped," "L-shaped," round, oval, etc., as is appropriate for a particular application. A plurality of light sources (or other micro-electronic circuits) 192 are mounted on opposite surfaces of flexible substrate 196. Electrical power and/or signals are conveyed to each of light sources 192 (or other microcircuits) over leads 194, which are coupled to electrical traces disposed internally (not shown) between opposite outwardly facing surfaces of substrate 196.

FIG. 18 illustrates how flexible sheet probe 190 is folded transversely into three layers to reduce the cross-sectional width of the resulting package, thereby permitting the flexible sheet probe to be more readily inserted into a treatment site through an access incision or internal body passage having a limited transverse dimension, e.g., through an incision less than two cm. in length. After the flexible sheet probe is folded in a tri-fold configuration 198 as shown in FIG. 18, a suture 200 is used to restrain it, preventing flexible sheet probe 190 from prematurely unfolding prior to its placement at a treatment site.

FIGS. 19 and 20 illustrate how a flexible sheet probe 196' that is formed of a elongate quadrilateral-shaped flexible substrate is folded lengthwise into three layers and restrained for insertion to a treatment site within a patient's body. In FIG. 19, a hairpin-shaped clip 204 is inserted over folded flexible sheet probe 196' to restrain it in a tri-fold configuration 198'. Similarly, in the embodiment shown in FIG. 20, a rectangular clip 206 having an internal opening sized to fit over tri-fold configuration 198' retains the folded state until the folded flexible sheet probe has been inserted into the treatment site.

FIG. 21 illustrates how, having removed the restraint (i.e., hairpin-shaped clip 204 or rectangular clip 206), the flexible sheet probe is unfolded within a space 214 that is disposed between layers of tissue 210, to apply PDT or other medical treatment or diagnostic procedure to an adjacent tumor or lesion 212. As indicated in FIG. 21, forceps 216 are used to grip opposite ends of flexible sheet probe 196', thereby enabling it to be unfolded so that it overlies tumor or lesion 212.

Disposition of Flexible Probes at Various Treatment Sites

In FIGS. 22–28, use of a flexible sheet probe 220 is illustrated. Flexible sheet probe 220 comprises a flexible substrate 222, which includes light sources and/or other micro-electronic circuitry mounted thereon in contact with conductive traces (none of which are shown). The flexibility of flexible sheet probe 220 facilitates its insertion in a treatment site inside a patient's body using a laparascopic procedure. Flexible sheet probe 220 is preferably rolled into concentric cylindrical layers around a cylinder template 228.

The roll of flexible substrate 222 is then restrained inside a sleeve 226, generally as shown in FIGS. 22–25.

A push rod 240 is used to insert the rolled flexible sheet probe retained by sleeve 226 through a guide tube 238. The guide tube is surgically positioned so that it extends through a cutaneous or other tissue layer 232 to access an internal treatment site 230. In addition, an instrument guide 234 and a laparascopic tube 236 are inserted through cutaneous or other tissue layer 232 from opposite sides of guide tube 238 so that their distal ends are disposed adjacent treatment site 230. Flexible sheet probe 220 will be deployed and unrolled to administer PDT or other medical therapy at treatment site 230.

In FIG. 27, laparascopes 241 are inserted through laparascope tube 236 and guide tube 234. Forceps 244 are then used to grasp cylinder template 228 and sleeve 226 to enable the sleeve to be withdrawn from rolled flexible substrate 222. Push rod 240 is also withdrawn through guide tube 238. Eye pieces 242, which are provided on each of the two laparascopes 241, enable the operator to manipulate rolled flexible substrate 222 and sleeve 226 during this procedure. Next, as shown in FIG. 28, forceps 246 are inserted through guide tube 238 to grasp sleeve 226, withdrawing it from treatment site 230. In addition, laparascopes 241 are used to unroll flexible substrate 222 at treatment site 230, thereby preparing it to administer PDT or other medical therapy. Although this step is not shown, forceps 246 are also used to withdraw template 228 through guide tube 238.

A cylindrical configuration for a flexible sheet probe 250 is shown in FIGS. 29–32. This embodiment comprises a flexible substrate 252 that is loosely rolled into a cylinder defining a passage 248 in the center of the cylinder through which fluids can readily flow when the flexible sheet probe is disposed within a body lumen. Disposed on an outer surface of flexible sheet probe 250 are a plurality of light sources 256, which are arranged in a closely spaced-apart array so that light emitted thereby irradiates the surface of a tumor (or other abnormal tissue) 258. Tumor 258 is disposed on the interior of a lumen 260. Lumen 260 may, for example, comprise a patient's esophagus or a blood vessel. A lead 254 conveys electrical current from a remote site, to energize the light sources and may optionally include additional conductors for conveying other signals to or from other types of micro-electronic circuitry mounted on flexible substrate 252.

Figure 30:
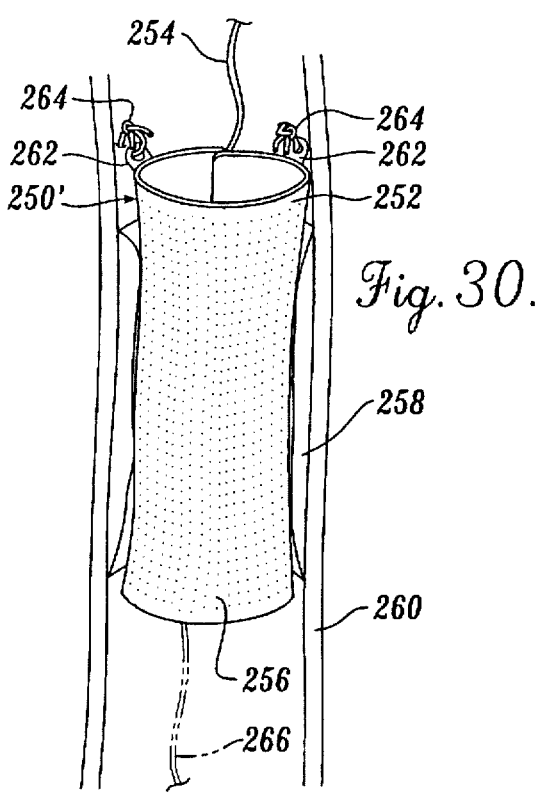
FIG. 30 is the sectional view of the internal passage showing the flexible probe held in position by sutures that connect loops on the flexible substrate to interior surfaces of the passage.

In FIG. 30, a flexible sheet probe 250' is illustrated that includes two loops 262 along one edge. Sutures 264 are passed through the loops in a laparascopic or endoscopic procedure, to secure the flexible sheet probe fixed adjacent tumor 258 on the interior of lumen 260. Optionally, a restraint line 266 may be attached to the opposite end of flexible sheet probe 250', further securing the flexible sheet probe fixed at the treatment site within passage 260.

One of the advantages of flexible sheet probes 250 and 250' is their characteristic elasticity that causes them to expand outwardly to a larger diameter as tumor 258 shrinks in response to the PDT or other therapy provided by the flexible sheet probe. Consequently, the light sources (or other micro-electronic circuits) mounted on flexible substrate 252 continue to remain in close proximity to the surface of the tumor as it contracts in response to the therapy.

Figure 30A:
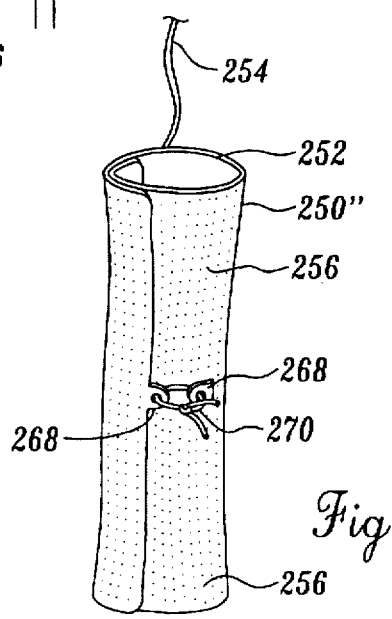
FIG. 30A is an isometric view of the rolled flexible probe, restrained by a suture that holds opposite ends of the rolled configuration in place.

In FIG. 30A, a further alternative flexible sheet probe 250" is illustrated. This embodiment includes loops 268 formed on flexible substrate 252, so that the loops are disposed proximate to each other when the flexible substrate is elastically formed into a cylinder. A suture 270 connects loops 268 to restrain the flexible substrate in the relatively small diameter, cylindrical configuration for placement at an internal treatment site. Suture 270 is then cut, enabling the characteristic elasticity of flexible substrate 252 to increase the diameter of the cylindrical shape so that it conforms to the internal diameter at the treatment site.

Figure 31:
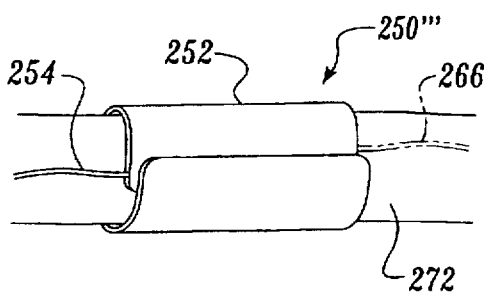
FIG. 31 is an isometric view of the fourth embodiment of the flexible probe rolled around a body lumen having a first cross-sectional size.
Figure 32:
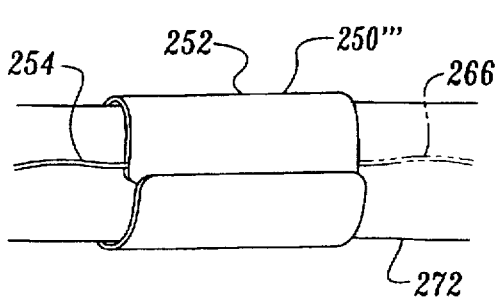
FIG. 32 is an isometric view of the fourth embodiment of the flexible probe rolled around a body lumen having a second cross-sectional size, showing how the rolled diameter of the flexible probe increases to accommodate physiological changes at a treatment site.

In FIGS. 31 and 32, a flexible sheet probe 250''' is illustrated having a plurality of light sources (not shown) on its inner surface. This embodiment is intended for use in treating the external surface of a blood vessel 272 (or other organ lumen) about which cylindrical form 250''' is placed. Again, a restraint line 266 is optionally provided to hold the flexible probe in position at the treatment site, in opposition to an opposing force applied through lead 254. As shown in FIG. 32, flexible sheet probe 250''' is formed into a tight cylindrical shape, which is the relaxed configuration of the flexible substrate. Because of the characteristic elasticity of the flexible substrate, the flexible sheet probe readily changes diameter to compensate for changes in the diameter of blood vessel 272 or other organ lumen about which its cylindrical shape is disposed. For example, as shown in FIG. 32, blood vessel 272 has a larger diameter than it does in FIG. 31, so that the overlap of opposite ends of flexible substrate 252 is less in FIG. 32 for the larger diameter blood vessel than it is in FIG. 31 for the smaller diameter blood vessel. As a result, the light sources or other electronic circuits mounted on the inner surface of the flexible sheet probe remain in intimate contact with the outer surface of the blood vessel as its diameter changes.

Figure 33:
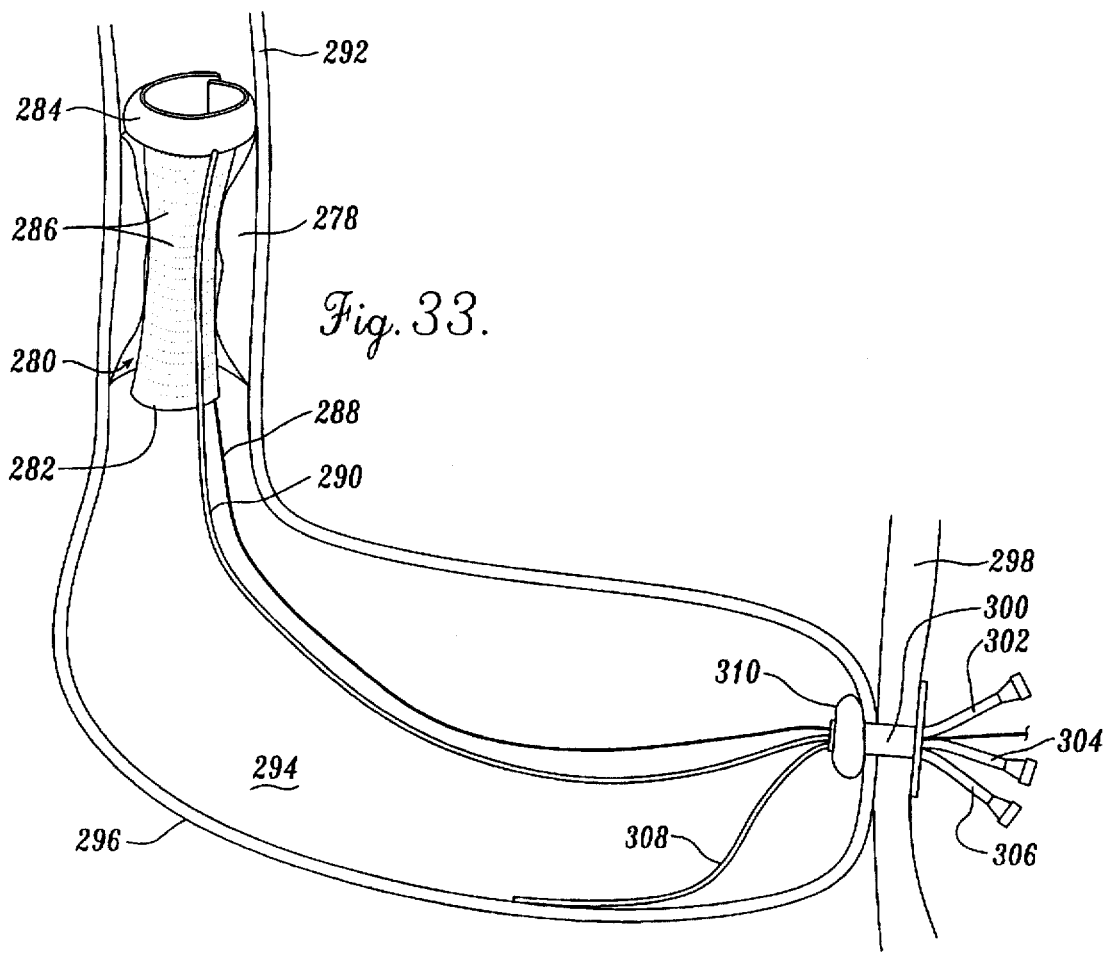

Turning now to FIG. 33, yet a further flexible sheet probe 280 having a normal cylindrical shape is illustrated for use in applying PDT to a tumor or lesion 278 disposed on the inner surface of an esophagus 292, at a point immediately adjacent to a stomach 294. Fluids flowing through esophagus 292 readily pass through the center of flexible sheet probe 280 and into stomach 294. A plurality of light sources 286 are disposed in spaced-apart array on a flexible substrate 282 that comprises flexible sheet probe 280. An upper end of flexible substrate 282 includes a balloon cuff 284, which is used to secure flexible sheet probe 280 in place, to administer PDT to the tumor.

An opening in a wall 296 of stomach 294 is aligned with a corresponding opening through a cutaneous layer 298 for insertion of a gastrostomy tube 300. A restraint balloon 310, which is disposed at the inner end of the gastrostomy tube, holds it in place and retains wall 296 of the stomach in position against the inner surface of cutaneous layer 298.

Passing through gastrostomy tube 300 are fluid lines 302, 304, and 306. Fluid line 302 is used to supply compressed air to inflate restraint balloon 310. Fluid line 304 is coupled in fluid communication with balloon cuff 284 through a fluid line 290 that extends from the balloon cuff through stomach 294. The balloon cuff is inflated using compressed air conveyed through fluid lines 290 and 304. Fluid line 306 connects to an internal fluid line 308 within stomach 294 that is used for aspirating fluid from the stomach or for adding medicaments. In addition, a lead 288 conveys electrical power to flexible sheet probe 280 to energize light sources 286 and can also be used for conveying signals to and from other micro-electronic circuitry mounted on flexible substrate 282. A flexible sheet probe 280' is illustrated with balloon cuff 284 inflated in FIG. 34, and with the balloon cuff deflated, in FIG. 35.

FIGS. 36 and 37 illustrate an alternate approach for positioning flexible probe 100 at a gastroesophageal junction 318 to provide PDT to a tumor 320 that is disposed at that point. In this approach, flexible probe 100 is inserted through the nasal passage of a patient 314, threaded through the patient's esophagus 292, and positioned so that the light emitting sources 102 are disposed adjacent tumor 320.

Yet a further alternative embodiment for positioning a flexible probe 100' adjacent tumor 320 is illustrated in FIGS. 38 and 39. Flexible probe 100' includes a restraint line 322 that extends through a nasal passage 324, while a lead 316 extends from the interior of the patient's stomach through gastrostomy tube 300 to an external power supply 326. Restraint line 322 is encapsulated within the clear biocompatible sheath 106 of flexible probe 100'.

It may be desirable to treat tumors and lesions that are disposed inside either the small or large intestine of a patient. In FIG. 40, an elastomeric bullet 330 is affixed to the distal end of flexible probe 100 using either a suture 332 or an elastic band that compresses the elastomeric bullet about the outer diameter of the flexible probe. Elastomeric bullet 330 has a substantially larger cross-sectional area than that of flexible probe 100, so that the natural peristalsis occurring within the small and large intestine advances the flexible probe from the stomach to a desired treatment site in the bowel. Once the flexible probe reaches the treatment site, suture or elastic band 332 is cut using an endoscopic procedure, and the elastomeric bullet is carried through the intestine and exits the patient's body during a normal bowel movement or is extracted endoscopically.

With reference to FIG. 41, a lead 316 connected to flexible probe 100 extends from the treatment site through the patient's large bowel 346 and small bowel 344, exiting stomach 294 through gastrostomy tube 300. To ensure that flexible probe 100 remains fixed at the treatment site where a tumor or lesion 352 is disposed on the internal surface of large bowel 346, loops 348 are attached with sutures 350 to the tissue of the bowel. An endoscope or colonscope is employed to place the sutures.

A disadvantage of the approach illustrated in FIG. 41 is the relatively long length required for lead 316, which must extend from the treatment site disposed near the lower end of large bowel 346 into stomach 294. The total length of lead 316 may easily exceed 25–30 feet. In FIG. 42, an alternative approach is shown, which employs a Bishop-Koop procedure to create an enterocutaneous fistula by transecting large bowel 346 at a point immediately above and adjacent to tumor 352. Sutures 356 are placed to connect the lower portion of the bowel to a new opening 354 made in the wall of the upper portion of the large bowel, adjacent the transection in the upper portion of the large bowel. A transected end 358 of the upper portion of the large bowel is then attached by sutures 360 to an opening 362 in abdominal wall 340, thereby enabling a relatively short lead 316 to exit the patient's body. Waste matter passing through large bowel 346 will continue to be moved through both sections of the transected bowel by peristalsis.

A flexible probe 370 having loops 376 disposed at each end is shown in FIG. 43. This embodiment illustrates an application in which the flexible probe is helically coiled around an artery 380 and secured at each end with sutures 378 that fasten loops 376 to adjacent tissue. A lead 372 extends from one end of the flexible probe to a power supply 374. Flexible probe 370 can thus be used, for example, in applying PDT to treat arteriosclerotic deposits inside artery 380 within the region about which the flexible probe is coiled. Light emitted by the light sources in the flexible probe is transmitted through the wall of the artery and absorbed by photoreactive dye-perfused arteriosclerotic deposits, causing the deposits to breakdown.

A flexible sheet probe 390 is shown in FIG. 44 for use in effecting PDT treatment of a congested coronary artery 398. The four corners of flexible sheet probe 390 are sutured to the pericardium lining around a heart 396 so that a flexible substrate 392 is disposed inside the pericardium lining. Since the pericardium lining is opaque and does not readily transmit light, the pericardium lining must be incised so that the flexible sheet probe can be disposed adjacent the coronary artery being treated and molded around the curved surface of the heart. Light emitted by the light sources mounted on the flexible probe thus passes into the interior of the coronary artery. A lead 394 extends from flexible substrate 392 to a remote power source that supplies electrical current to energize the light sources. FIG. 45 illustrates arteriosclerotic deposits 402 in a blood vessel or coronary artery that may be treated using PDT administered with the present invention.

Fabricating Flexible Probes

For manufacturing flexible probes that are elongate, such as flexible probes 100 and 108, a plurality of strips of flexible substrate are preferably produced from a larger flexible substrate 412, as shown in FIG. 46. In an initial prototype of the present invention, the overall outer dimensions of the flexible substrate are approximately 3.9"×4.6"; however, these dimensions are not in any way limiting, since the flexible substrate can be made in almost any size desired. A plurality of pairs of parallel conductive traces 414a and 414b are applied to the surface of flexible substrate 412 using conventional photolithography techniques, defining a plurality of flexible substrate strips 410 that can be cut from flexible substrate 412 after light emitting sources or other micro-electronic circuitry are mounted thereon. In the initial prototype of the present invention, the flexible traces comprise a layer of wire bondable soft gold electroplate about 0.00003" thick over a layer of sulfamate nickel electroplate about 0.0001" thick, over one ounce copper that is applied to the polyimide film comprising the flexible substrate. While substantially narrower conductive traces can readily be formed, conductive traces 414a and 414b in the prototype are about 0.025" wide and are spaced about 0.005" apart. Other techniques for producing conductive traces that are flexible and other materials comprising the conductive traces can alternatively be used to make the present invention, as are well known in the prior art. Examples of prior art flexible circuit laminates and procedures for making the flexible circuit laminates and applying conductive traces are disclosed in U.S. Pat. Nos. 4,647,508 and 4,634,631 (Gazit et al.), which are assigned to Rogers Corporation.

In FIG. 47, a flexible substrate strip 410 is illustrated (enlarged), wherein a plurality of spaced-apart "Xs" mark locations for mounting the light emitting sources or other micro-electronic circuits on conductive traces 414a and 414b. It is also contemplated that additional conductive traces may be provided for more complex electronic circuitry, for example, to convey signals and for interconnections, as is well known to those of ordinary skill in the art.

A line 416 disposed in the middle of flexible strip 410 indicates where the strip is to be either cut or folded to create the flexible probe shown in FIG. 48. In this flexible probe, a plurality of LEDs 418 are attached to conductive traces 414a on flexible substrate 412, which is cut on line 416. The two portions of the flexible substrate are then bonded together (back-to-back) to create a double thick flexible substrate. Fly wires 420 connect terminals 424 on LEDs 418 to conductive traces 414b. The fly wires are preferably ultrasonically bonded, but may alternatively be soldered, or otherwise attached to terminals 424 and conductive traces 414b. Conductive epoxy 422 adherently attaches the other terminals of LEDs 418 to conductive traces 414a, as shown in FIG. 49. Transparent flexible envelope 106 encloses the assembly, protecting LEDs 418 and fly wires 420 from damage as the flexible probe is flexed or bent during use.

Yet another configuration for a flexible probe 460 is illustrated in FIG. 53. In this configuration, light sources 470 (or other micro-electronic circuitry), are mounted between conductive traces 466 and 468 that are applied to the surface of flexible substrate strips 462. The conductive traces are adherently secured to terminals on the light sources (or other types of micro-electronic circuitry) by conductive epoxy layers 472, as shown in FIG. 54. A transparent, biocompatible flexible polymer envelope 464 protects the assembly and provides additional strength. Light emitted by light sources 470 passes through flexible substrate strips 462 and through envelope 464.

A serpentine flexible sheet probe 480 is illustrated in FIG. 55. In this embodiment, a pair of conductive traces 488 and 490 define two serpentine paths that are generally equidistant from each other and are applied to a flexible substrate 482. Leads 484 and 486 respectively connect to the conductive traces so that electrical current can be supplied to energize light sources 492. As shown in FIG. 56, fly wires 494 electrically couple light sources 492 to conductive traces 488. The light sources are also adhesively and electrically connected to conductive traces 490. The resulting flexible sheet is encapsulated within an envelope of a clear biocompatible polymer material 496, as indicated by the dash lines surrounding the flexible substrate and light source.

Referring now to FIGS. 57 and 58, an alternative approach for coupling a light sources (or other type of electronic microcircuit) to conductive traces 504 and 506 that are applied to a flexible substrate strip 502 is illustrated. In this approach, the light sources preferably comprise two different types of LEDs 508 and 508' that emit light having different characteristic wavelengths, e.g., 640 nm and 720 nm, respectively. The LEDs are mounted on the flexible substrate strip, between conductive traces 504 and 506, with terminals on the LEDs disposed immediately adjacent one of the conductive strips. Although only one LED 508' is shown, it will be understood that LEDs 508 alternate with LEDs 508' along the flexible substrate strip. Alternative configurations for mounting the two types of LEDs are clearly contemplated, for example, mounting two LEDs 508, followed by two LEDs 508' along the flexible substrate strip, and various patterns or arrays of the different LEDs can be provided on flexible substrate sheets.

A fly wire 510 connects a terminal 514 disposed on one side of each LED 508 to conductive trace 506, and a drop of conductive epoxy 512 connects the terminal on the opposite side of each LED 508 to conductive trace 504. Alternatively, a corresponding drop of conductive epoxy may be used in lieu of fly wire 510 to connect terminal 514 to conductive trace 506. Similarly, fly wire 510 (or a drop of conductive epoxy) connects terminal 514 disposed on light source 508' to conductive trace 504, and drop of conductive epoxy 512 connects the opposite side terminal of light source 508' to conductive trace 506. Thus, the polarities of the terminals on LEDs 508 are opposite those of LEDs 508'. Consequently, for a particular polarity of voltage applied between conductive traces 504 and 506, only one of the two different types of LEDs are energized to emit light at the characteristic wavelength of that type of LED. Accordingly, by selecting the polarity of the voltage applied to energize the LEDs, the wavelength of LEDs 508 or 508' can be selected. The other type of LEDs will not be energized until the applied voltage polarity is reversed. An advantage of this configuration is that PDT can be selectively administered with light at one of two different wavelengths. Two different photoreactive agents that absorb light at the characteristic wavelengths of LEDs 508 and 508' will typically be applied to the treatment site to enable the medical practitioner controlling the PDT to select the wavelength that appears most effective in the treatment. Just as a plurality of chemotherapy regimens are often more effective in destroying cancerous tissue, a plurality of different wavelengths may prove more effective in PDT of abnormal tissue. The practitioner may select the more effective wavelength or may elect to administer light at alternating wavelengths to the treatment site.

Preferably, flexible substrate strip 502 is transparent to light emitted by LEDs 508 and 508'. Although not shown, this embodiment will typically be enclosed in a transparent biocompatible polymer envelope, just as the other embodiments described above are.

In FIG. 59, details of a flexible sheet probe 520 are illustrated. In this embodiment, a flexible substrate comprising a generally planar and quadrilateral-shaped sheet is provided with a plurality of conductive traces 524 and 526, as pairs of strips that extend generally parallel to each other across a flexible substrate 522. All of the strips comprising conductive traces 524 are electrically connected to a lead 528, and all of the strips comprising conductive traces 526 are electrically connected to a lead 530. Depending upon the spacing between conductive traces 524 and 526, the various techniques shown above can be used for mounting light sources or other types of micro-electronic circuitry to the pairs of conductive traces. After such devices are mounted and electrically connected to the conductive traces, the flexible substrate probe is enclosed within a transparent, biocompatible polymer envelope 532.

To focus light emitted from light sources mounted on any of the flexible probes described above, it is contemplated that a reflector 544 can be mounted within or adjacent to each light source 542, as shown in FIG. 60, to facilitate reflecting or focusing light emitted by the light source. In this Figure, conductive epoxy adhesively mounts light source 542 and reflector 544 to conductive trace 524 and provides an electric path between the terminal of the light source and the conductive trace. Similarly, a fly wire 548 electrically connects the other terminal of the light source to conductive trace 526. It is also contemplated that a reflective surface can be fabricated within the light source, to facilitate focusing light emitted by the light source.

Flexible Probe System

As noted repeatedly above, flexible probes made in accordance with the present invention can be used for other purposes, but are primarily disclosed in connection with providing PDT. In FIG. 50, LEDs or other types of light source(s), and/or other types of micro-electronic circuits are provided electrical current to energize the devices through power leads 316 from a power supply 326, which may be either remotely located outside the patient's body, may comprise a battery mounted on/adjacent the flexible probe or at a remote site within the patient's body, or may be coupled electromagnetically or through an RE signal, to an external source of power. It is also contemplated that power can be supplied from an external IR light source (not shown) producing IR light that passes through the cutaneous layer and is converted by an IR detector (not shown) into electrical current supplied to the flexible substrate. FIG. 50 is a block diagram generally illustrating the flexible probe system.

In FIG. 51, flexible probe 100 is shown with leads 316 that are intended to extend outside the patient's body and thus terminate in connectors 428 for direct connection to an external power supply 326. However, as noted above, electrical power and signals can be conveyed between the flexible probe and an external device, across a cutaneous layer 452 and without a direct connection, as illustrated in FIG. 52. In this Figure, an LED array 436 and photodetectors 438 are mounted on a flexible probe 440. The flexible probe is directly connected to a rectifier 434. Rectifier 434, an optional rechargeable battery 435, a receiver coil array 430, a driver circuit 442, and a telemetry transmitter 444 are preferably disposed together within the patient's body, apart from the treatment site. Rectifier 434 is electrically connected to receiver coil array 430 and full-wave rectifies alternating current output from the receiver coil array, producing electrical current that may be used to charge optional rechargeable battery 435. If rechargeable battery 435 is used, the power stored therein is subsequently supplied to the flexible probe to energize the light source(s), and/or other micro-electronic circuitry mounted thereon. Receiver coil array 430 includes at least one receiver coil (not shown) that is energized by electromagnetic or RF energy transmitted from an external power coil 448 disposed outside the patient's body, adjacent cutaneous layer 452, opposite receiver coil array 430. Electrical energy is supplied to power coil 448 from a power supply 450. The power supply is energized from a conventional 60 Hz, 120 volts alternating current line (not shown).

Photodetectors 438 are included on flexible probe 440 to monitor the fluorescence by cells treated with a photoreactive agent at a treatment site, to determine whether additional photoreactive agent should be added to the treatment site and/or to determine the efficacy of the PDT. The extent of such fluorescence is a function of the amount of photoreactive agent absorbed by abnormal cells, and if recently perfused into the treatment site, indicates the extent of abnormal cells remaining. The photodetectors mounted on a second flexible probe (not shown) disposed on an opposite side of the treatment site from that at which a flexible probe comprising a light source can also be used to monitor light transmission through the treatment site to determine the amount of photoreactive agent present and to monitor the efficacy of the system in applying the PDT.

Signals developed by photodetectors 438 are conveyed to a driver circuit 442, which provides a suitable signal to drive telemetry transmitter 444. In response to the drive signal, telemetry transmitter 444 produces an RF signal that is indicative of the output from the photocells mounted on the flexible probe. The RF signal developed by telemetry transmitter 444 is conveyed across cutaneous layer 452 to an external telemetry receiver 446, which indicates the level of the signal to an operator.

For embodiments of the flexible probe in which it is preferable to provide power for the light sources or other micro-electronic circuits mounted on the flexible probe through electromagnetic coupling, as opposed to directly through leads that extend externally outside the patient's body, either of two types of coils can be used, as shown in FIGS. 61 and 62. In FIG. 61, a receiver coil 552 comprises a plurality of turns of conductive lead 554. Receiver coil 552 can be located at some distance from the treatment site within the patient's body, and is disposed immediately under and adjacent a cutaneous layer 550. To provide electrical energy to the flexible probe disposed at the treatment site, a transmitter coil 556 comprising a number of turns of a conductive lead 558 that is connected to an external power supply (not shown in FIG. 61) is disposed on the outer surface of cutaneous layer 550, immediately adjacent receiver coil 552. An alternating current applied by the external power supply develops an electromagnetic field in transmitter coil 556 that couples to receiver coil 552, causing a corresponding alternating current to flow in the receiver coil. This alternating current is rectified using a full wave rectifier (such as rectifier 434 shown in FIG. 52), which may be included within the flexible probe, or alternatively, disposed at receiver coil 552.

In a related scheme, a transmitter coil 580 comprising a ferrite core 582 (or a core of another material having a relatively high magnetic permeability) that is generally "C"-shaped is coupled through leads 558 to an external power supply (not shown), which supplies an alternating current to helical conductive coils 584 that are wrapped around a ferrite core 582. The alternating current flowing through conductive coils 584 develops an electromagnetic field that is coupled to a receiver coil 590. Receiver coil 590 is disposed immediately opposite transmitter coil 580, inside the patient's body, under cutaneous layer 550. Receiver coil 590 also comprises a C-shaped ferrite core 592, around which is helically coiled a conductor 594, which is coupled to leads 554 to convey electrical current to the remotely located flexible probe that is disposed at the treatment site within the patient's body. Transmitter coil 580 and receiver coil 590 are oriented with their respective ferrite cores 582 and 592 aligned, so as to maximize flux linkage between the ferrite cores. These coils are substantially more efficient at transferring electromagnetic energy than transmitter coil 556 and receiver coil 552, since the latter are limited by the relatively low magnetic permeability of air rather than the much greater magnetic permeability of the ferrite cores.

It is contemplated that various other configurations and arrays of transmitter and receiver coils can be used to supply power to energize the electronic components inside the patient's body and mounted on the flexible probe. It is also contemplated that the receiver coil can be mounted on the flexible probe in those cases where the treatment site is disposed immediately adjacent cutaneous layer 550.

FIG. 63 illustrates a panel 604 of infrared LEDs 606 that is disposed against the external surface of cutaneous layer 550. Infrared LEDs 606 are energized with electrical current from the external power supply through leads 558. Immediately adjacent panel 604, inside cutaneous layer 550, is disposed a panel 600 of infrared sensitive photovoltaic cells 602. In response to the infrared light received from panel 604, photovoltaic cells 602 produce an electrical current that is supplied to the flexible probe (or a storage battery) through leads 554.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. Apparatus for effecting a medical treatment at an internal site within a patient's body, comprising:
   (a) a flexible substrate;
   (b) a plurality of conductive traces affixed to the flexible substrate, said conductive traces being sufficiently flexible to bend with the flexible substrate without breaking or separating from the flexible substrate as the flexible substrate is flexed during its insertion into a patient's body and advanced to the internal site;

(c) an electrical device disposed on the flexible substrate and coupled to the plurality of conductive traces, said electrical device being carried by the flexible substrate for disposition at the internal site;

(d) a biocompatible, flexible envelope hermetically enclosing the flexible substrate, the plurality of conductive traces, and the electrical device; and (e) a plurality of electrical leads connected to the conductive traces, said electrical leads being adapted to couple to a source of electrical power in order to energize the electrical device, and being operative to carry signals between the electrical device and a different location.

2. The apparatus of claim 1, wherein the flexible substrate comprises a strip having a thickness, a width, and a length, said thickness of the strip being substantially less than its width, and said width of the strip being substantially less than its length.

3. The apparatus of claim 1, wherein said electrical device comprises at least one micro-electronic circuit.

4. The apparatus of claim 1, wherein the flexible substrate comprises a sheet having a thickness and a width, said thickness of the sheet being substantially less than its width.

5. The apparatus of claim 4, wherein the flexible substrate is sufficiently flexible to be rolled into a tubular shape for insertion into the patient's body, said tubular shape having a substantially smaller transverse cross-sectional dimension than the width of said flexible substrate, prior to being rolled.

6. The apparatus of claim 1, wherein the flexible substrate is sufficiently flexible to be folded into a more compact shape without damage.

7. The apparatus of claim 6, wherein the flexible substrate is folded at about a midpoint, being thereby adapted to form a loop that is collapsed for insertion into the patient's body, said loop opening to form an open loop at the internal site.

8. Apparatus for administering light to a treatment site within a patient's body, comprising:

(a) a flexible substrate serving as a support;

(b) conductive traces affixed to the flexible substrate, said conductive traces being sufficiently flexible to bend with the flexible substrate without breaking or separating from the flexible substrate, thereby enabling the apparatus to be flexed when being inserted into the patient's body and when being disposed at the treatment site within the patient's body;

(c) at least one light source electrically coupled to the conductive traces and mounted to the flexible substrate;

(d) a plurality of electrical leads connected to the conductive traces, said electrical leads being adapted to couple to a source of electrical power in order to energize said at least one light source to emit light that is incident on the treatment site within the patient's body; and (e) a flexible envelope of a transparent material that hermetically encloses said at least one light source, the conductive traces, and the flexible substrate, said flexible envelope transmitting light emitted from said at least one light source to the treatment site.

9. The apparatus of claim 8, wherein the flexible substrate comprises a sheet that is generally quadrilateral in shape.

10. The apparatus of claim 8, further comprising a plurality of light sources that are spaced apart on the flexible substrate, forming an array.

11. The apparatus of claim 10, wherein the flexible substrate is folded to form a flattened loop for insertion into the patient's body, said flattened loop expanding into an open loop when the flexible substrate is disposed at the treatment site.

12. The apparatus of claim 8, wherein the flexible substrate is curved, so that when inserted into the patient's body for use at a treatment site comprising a lumen, the flexible substrate conforms to a shape of the lumen, with said at least one light source illuminating a surface of the lumen.

13. The apparatus of claim 8, wherein the flexible substrate is rolled to minimize its cross-sectional size for insertion within the patient's body and disposition at the treatment site, said flexible substrate being unrolled to administer light to the treatment site.

14. The apparatus of claim 8, wherein the flexible substrate is folded to reduce its cross-sectional area relative to a width of the flexible substrate, adapting the flexible substrate for insertion within the patient's body and disposition at the treatment site, where the flexible substrate is then unfolded to administer light to the treatment site.

15. The apparatus of claim 8, further comprising an electromagnetic receiver that is connected to the electrical leads, said electromagnetic receiver being adapted to electromagnetically couple to a source of electrical power that is disposed outside the patient's body, and thereby to provide an electrical current for energizing said at least one light source.

16. The apparatus of claim 15, wherein the electromagnetic receiver comprises an electromagnetic coil.

17. The apparatus of claim 15, wherein the electromagnetic receiver comprises a radio frequency receiver that receives radio frequency energy from an external source.

18. The apparatus of claim 8, wherein the flexible substrate has a predetermined configuration when not constrained and is thus adapted to be inserted into a treatment site in a restrained configuration and brought into contact with tissue at the treatment site so that said tissue contacts the flexible substrate and maintains the flexible substrate in its restrained configuration, a characteristic elasticity of said flexible substrate adapting it to change shape and flex radially outwardly toward its unconstrained configuration as any abnormal tissue at the treatment site shrinks in response to light emitted by said at least one light source.

19. The apparatus of claim 8, further comprising a catheter through which the flexible substrate is guided to the treatment site inside the patient's body.

20. The apparatus of claim 8, wherein the source of electrical power comprises a battery.

21. The apparatus of claim 8, further comprising a plurality of light sources, including two different sets of light sources, each set of light sources when energized, emitting light having a characteristic peak wavelength substantially different than the characteristic peak wavelength of the light emitted by the light sources comprising the other set.

22. The apparatus of claim 21, wherein each set of light sources is selectively energized to determine the wavelength of the light emitted by the apparatus.

23. The apparatus of claim 21, wherein some of the light sources are coupled to the conductive traces with a polarity opposite that of others of the light sources, so that a polarity of the voltage supplied to the conductive traces determines which light sources are energized.

24. The apparatus of claim 8, further comprising a source of infrared light and an infrared light photovoltaic receiver, said source of infrared light being adapted to couple to a power supply and when energized thereby, to emit infrared light that passes transcutaneously into a patient's body to energize the infrared light photovoltaic receiver, said infrared photovoltaic receiver producing an electric current in response thereto and being coupled to the electrical leads to energize said at least one light source.

25. A method for effecting a medical treatment at an internal site within a patient's body, comprising the steps of:

(a) providing an electrical device that is mounted on a flexible substrate in contact with a plurality of conductive traces disposed on the flexible substrate, said electrical device, said plurality of conductive traces, and said flexible substrate being hermetically sealed within a biocompatible, flexible envelope that encloses the electrical device, the plurality of conductive traces, and the flexible substrate;

(b) supplying electrical power to the electrical device through the conductive traces;

(c) inserting the flexible substrate and electrical device into the patient's body by flexing the flexible substrate to reduce its size in at least one dimension or to enable it to pass through a curved lumen; and (d) positioning and deploying the flexible substrate and electrical device at the internal site to facilitate use of the electrical device.

26. The method of claim 25, wherein the flexible substrate comprises a strip having a thickness, a width, and a length, said thickness of the strip being substantially less than its width, and said width of the strip being substantially less than its length.

27. The method of claim 25, wherein said step of providing the electrical device comprising the step of mounting at least one micro-electronic circuit on the flexible substrate.

28. The method of claim 25, wherein the flexible substrate comprises a sheet having a thickness and a width, said thickness of the sheet being substantially less than its width; said step of providing the electrical device comprising the step of mounting at least one micro-electronic circuit on the sheet.

29. The method of claim 25, wherein the flexible substrate is sufficiently flexible to be rolled into a tubular shape for insertion into the patient's body, said step of inserting including the step of rolling the flexible substrate into a tubular shape having a substantially smaller transverse cross-sectional dimension than the width of said flexible substrate prior to being rolled.

30. The method of claim 25, wherein the flexible substrate is sufficiently flexible to be folded, said step of inserting including the step of folding the flexible substrate into a shape having a substantially smaller transverse cross section than said flexible substrate prior to being folded.

31. The method of claim 30, further comprising the step of folding the flexible substrate at about a midpoint, thereby forming the flexible substrate in a collapsed loop for insertion into the patient's body, wherein said step of positioning and deploying comprises the step of opening said collapsed loop to form an open loop at the internal site.

32. A method for administering light therapy to an internal treatment site within a patient's body, comprising the steps of:

(a) providing at least one light source mounted on a flexible substrate in electrical contact with conductive traces disposed on the flexible substrate, said at least one light source, said flexible substrate, and said conductive traces being hermetically sealed within a biocompatible flexible envelope that is generally transparent to light emitted by said at least one light source;

(b) supplying electrical power to said at least one light source through the conductive traces;

(c) inserting the flexible substrate and said at least one light source into the patient's body by flexing the flexible substrate to reduce a size of the flexible substrate in at least one dimension sufficiently to fit within an opening into the patient's body;

(d) positioning the flexible substrate at the treatment site; and (e) irradiating the treatment site with light emitted by said at least one light source to effect the light therapy.

33. The method of claim 32, wherein the step of inserting comprises the step of folding the flexible substrate, thereby enabling the flexible substrate and said at least one light source to be inserted into the patient's body through a lumen having a cross section that is smaller than a width of the flexible substrate prior to being folded.

34. The method of claim 32, wherein the step of inserting comprises the step of rolling the flexible substrate into a tubular shape to reduce its transverse size, thereby enabling the flexible substrate and said at least one light source to be inserted into the patient's body through a lumen having a cross-sectional dimension that is less than a width of the flexible substrate prior to the flexible substrate being rolled.

35. The method of claim 32, wherein the step of inserting comprises the step of bending the flexible substrate to enable the flexible substrate to pass through a curved lumen to reach the internal treatment site.

36. The method of claim 32, wherein the step of positioning the flexible substrate comprises the step of forming the flexible substrate around a surface contour of the internal treatment site within the patient's body.

37. The method of claim 32, wherein the step of positioning the flexible substrate comprises the step of bending the flexible substrate to enable it to fit within a body cavity, said cavity enclosing the internal treatment site within the patient's body.

38. The method of claim 32, further comprising the steps of securing the flexible substrate in a restrained configuration prior to inserting the flexible substrate into the patient's body, and after the flexible substrate is disposed at the treatment site, releasing the flexible substrate to deploy the flexible substrate in an unrestrained configuration at the internal treatment site.

39. The method of claim 32, further comprising the step of energizing said at least one light source using a power source that is external to the patient's body.

40. The method of claim 32, further comprising the step of energizing said at least one light source with an electrical current that is conveyed to the conductive traces through leads that extend outside the patient's body.

41. The method of claim 32, wherein said at least one light source mounted on the flexible substrate is enclosed within a flexible, transparent material.

42. The method of claim 32, wherein the step of inserting comprises the step of guiding the flexible substrate to the treatment site through a catheter.

43. The method of claim 32, wherein the step of positioning comprises the step of pulling the flexible substrate through a body lumen to the treatment site by applying force to a line that is coupled to the flexible substrate to move the flexible substrate.

44. The method of claim 32, further comprising the step of creating a transcutaneous opening into the patient's body for insertion of the flexible substrate.

45. The method of claim 32, further comprising the step of providing a balloon in fluid communication with a lumen that extends outside the patient's body, said balloon being inflated at an opening into an organ in which the internal treatment site is disposed, to restrain the flexible substrate within the organ at the internal treatment site.

46. The method of claim 32, wherein the step of positioning comprises the step of securing the flexible substrate in a fixed position at the internal treatment site within the patient's body.

47. The method of claim 32, further comprising the step of providing a plurality of light sources that are mounted on the flexible substrate, arranged in a spaced apart array.

48. The method of claim 47, wherein the plurality of light sources include two sets of light sources, each set of light sources emitting light having a characteristic peak wavelength that is substantially different than the characteristic peak wavelength of light emitted by the other set of light sources.

49. The method of claim 48, further comprising the step of selectively energizing only one of the sets of the light sources at one time.

50. The method of claim 48, further comprising the steps of coupling some of the light sources to the conductive traces with a different polarity than used to couple other of the light sources to the conductive traces; and, applying a voltage of a selected polarity to the conductive traces to selectively energize only the light sources coupled to the conductive traces so as to be energized by said voltage.

51. The method of claim 32, wherein the steps of supplying electrical power comprises the step of transmitting infrared light transcutaneously into a patient's body; receiving the infrared light inside the patient's body; and, converting the infrared light into an electrical current that is used to energize said at least one light source.

* * * * *